(12) United States Patent
MacLennan

(10) Patent No.: US 6,518,414 B1
(45) Date of Patent: Feb. 11, 2003

(54) MOLECULAR CLONING AND EXPRESSION OF G-PROTEIN COUPLED RECEPTORS

(76) Inventor: Alexander John MacLennan, 7811 NW 35th Place, Gainesville, FL (US) 32606

( * ) Notice: Subject to any disclaimer, the term of this patent is extended or adjusted under 35 U.S.C. 154(b) by 0 days.

(21) Appl. No.: 09/225,024

(22) Filed: Jan. 4, 1999

Related U.S. Application Data

(63) Continuation-in-part of application No. 08/760,936, filed on Dec. 6, 1996, now Pat. No. 5,856,443, which is a continuation of application No. 08/196,989, filed on Feb. 15, 1994, now Pat. No. 5,585,476.

(51) Int. Cl.[7] .............................................. C12N 15/12
(52) U.S. Cl. ..................... 536/23.5; 435/69.1
(58) Field of Search .................. 435/7.1, 7.2; 475/69.1; 530/350; 536/23.5

(56) References Cited

PUBLICATIONS

An et al. Identification of cDNAs encoding two G protein–coupled receptors for lysosphingolipids. FEBS Letters 417:279–282, 1997.*
Jackson. Structure and Function of G Protein Coupled Rerceptors. Pharmac. Ther. 50:425–442, 1991.*
Supplemental Information Disclosure Statement Under 37 CFR §§1.97 and 1.98 dated Mar. 14, 2002.
Declaration of Stephen Sims dated Nov. 8, 2001.
Yarden, Y.A. Ullrich (1988) "Growth Factor Receptor Tyrosine Kinases" Ann. Rev. Biochem. 57:443–478.
Devreotes, P. (1989) "Dictyostelium discoideum: A Model System for Cell–Cell Interactions in Development" Science 245:1054–1058.
Hanley, M.R. (1989) "Mitogenic neurotransmitters" Nature 340:97.
Zachary, I., P.J. Woll, E. Rozengurt (1987) "A Role for Neuropeptides in the Control of Cell Proliferation" Dev. Biol. 124:295–308.
Young, D., G. Waitches, c. Birchmeier, O. Fasano, M. Wigler (1986) "Isolation and Characterization of a New Cellular Oncogene Encoding a Protein with Multiple Potential Transmembrane Domains" Cell 45:711–719.
Gutkind, J.S., E.A. Novotny, M.R. Brann, K.C. Robbins (1991) "Muscarinic acetylcholine receptor subtypes as agonist–dependent oncogenes" Proc. Natl. Acad. Sci. USA 88:4703–4707.
Julius, D., T.J. Livelli, T.M. Jessell, R. Axel (1989) "Ectopic Expression of the Serotonin 1c Receptor and the Triggering of Malignant Transformation" Science 244:1057–1062.
Julius, D., K.N. Huang, T.J. Livelli, R. Axel, T.M. Jessell (1990) "The 5HT2 receptor defines a family of structurally distinct but functionally conserved serotonin receptors" Proc. Natl. Acad. Sci. USA 87:928–932.
MacLennan, A.J., G.D. Frantz, R.C. Weatherwax, N.J.K. Tillakaratne, A.J. Tobin (1990) "Expression of mRNAs That Encode D2 Dopamine Receptor Subtypes: Anatomical, Developmental, and Pharmacological Studies" Molec. Cell. Neurosci. 1:151–160.
Loy, E.Y., J.F. Elliott, S. Cwirla, L.L. Lanier, M.M. Davis (1989) "Polymerase Chair Reaction with Single–Sided Specificity: Analysis of T Cell Receptor σChain" Science 243:217–220.
Sanger, F., S. Nicklen, A.R. Coulson (1977) "DNA sequencing with chain–terminating inhibitors" Proc. Natl. Acad. Sci. USA 74:5463–5467.
Chirgwin, J.M., E. Przbyla, R.J. MacDonald, W.J. Rutter (1979) "Isolation of Biologically Active Ribonucleic Acid from Sources Enriched in Ribonuclease" Biochem. 18:5294–5299.
Okazaki (1993) "Molecular Cloning of a Novel Putative G Protein Coupled Receptor Expressed in the Cardiovascular System" Biochem. Biophys. Res. Comm. 190:1104–1109.

* cited by examiner

*Primary Examiner*—John Ulm
(74) *Attorney, Agent, or Firm*—Saliwanchik, Lloyd & Saliwanchik

(57) ABSTRACT

The subject invention pertains to cloning and expression of novel cDNAs which encode members of the G-protein coupled receptor superfamily of proteins. Polynucleotides which encode mammalian H218 protein are described. The invention also concerns methods for screening for ligands of H218 protein. The proteins and peptides of the subject invention can also be used to produce antibodies which can bind to the subject proteins. The polynucleotide molecules, proteins, and antibodies of the subject invention can be used in both diagnostic and therapeutic applications.

2 Claims, 13 Drawing Sheets

```
-155  CCCCCCCCCCCTGAGCACAGCCAACAGTCAGCCACTGGCTGTCCCGG
 -95  GGCGCAGACGCCAAGGCCACTCAGGCCAGGGACCCTGGCCCTAGCCAGTGCT
 -35  CAGTCCCATGGCCCCGGCCCCGGCCCACTGAGCCCACCATGGGCGGTTTATACTCAGAGTAC
                                          MetGlyGlyLeuTyrSerGluTyr    8

25  CTCAATCCTGAGAAGGTTCAGGAACACTACAATTACACCAAGGAGACGCTGGACATGCAG
      LeuAsnProGluLysValGlnGluHisTyrAsnTyrThrLysGluThrLeuAspMetGln  28

85  GAGACGCCCCTCCCGCAAGGTGGCCTCCGCTTCATCATTTATGTGTGCCATCGTG
      GluThrProSerArgLysValAlaSerAlaPheIleIleIleLeuCysAlaIleVal    48

145  GTGGAGAACCTTCTGGTCTAATCGCAGTGCCAGGAACAGCAAGTTCCACTCAGCCATG
      ValGluAsnLeuLeuValLeuIleAlaValAlaArgAsnSerLysPheHisSerAlaMet  68

205  TACCTGTTCCTCGGCAACCTGGCCAGCCTCCGACCTGCTGGCAGGCGTGGCCTTCGTGCC
      TyrLeuPheLeuGlyAsnLeuAlaSerAspLeuLeuAlaGlyValAlaPheValAla    88

265  AACACCTTGCTCTCCGGACCTGTCACCCTGTCCTTAACTCCCTTGCAGTGGTTTGCCGA
      AsnThrLeuLeuSerGlyProValThrLeuSerLeuThrProLeuGlnTrpPheAlaArg  108

325  GAGGGTTCAGCCTTCATCACGCTCTCTGCCTGGCCTCTTCAGCCTCCTGGCCATTGCCATC
      GluGlySerAlaPheIleThrLeuSerAlaSerValPheSerLeuLeuAlaIleAlaIle  128

385  GAGAGACAAGTGGCCATGCCAAGGTGGCCAAGGTCCAAGCTGTACGGCTGAGTGGATG
      GluArgGlnValAlaIleAlaAlaLysValLeuTyrGlySerAspLysSerCysArgMet  148

445  TTGATGCTCATTGGGGCCCTCTTGGCTGATATCGCTGATTCTGGCTGGCCTTGCCCATCCTG
      LeuMetLeuIleGlyAlaSerTrpLeuIleSerLeuIleLeuGlyLeuProIleLeu    168

505  GGCTGGAATTGTCTGGACCATCTGGAGGCTTGCTGCCCCCTCTATGCTAAG
      GlyTrpAsnCysLeuAspHisLeuGluAlaCysSerThrValLeuProLeuTyrAlaLys  188

565  CACTATGTGCTCTGCGTGGTCACCATCTCTCTGTCATCTTACTGGCTATCGTGGCCTTG
      HisTyrValLeuCysValValThrIlePheSerValIleLeuAlaIleValAlaAlaLeu  208
```

FIG. 1A

```
625   TACGTCCGAATCTACTTCGTAGTCCGCTCAAGCCATGCGGACGTTGCTGGTCCTCAGACG    228
      TyrValArgIleTyrPheValArgSerHisAlaAspValAlaGlyProGlnThr

685   CTGGCCCTGCTCAAGACAGTCACCATCGTACTGGGTGTTTCATCATCTGCTGGCTGCCG    248
      LeuAlaLeuLeuLysThrValThrIleValLeuGlyValPheIleIleCysTrpLeuPro

745   GCTTTTAGCATCCTCTCTCTTAGACTCTCTGCCCGGGCCCTGTCCCTGTCCTCTAC      268
      AlaPheSerIleLeuSerLeuAspSerThrCysProValArgAlaCysProValLeuTyr

805   AAAGCCCATTATTCTTTGCCTTCCACCCTCAACTCTGCTCAACCCTGTCATCTAT       288
      LysAlaHisTyrPhePheAlaThrLeuAsnSerLeuLeuAsnProValIleTyr

865   ACATGGCGTAGCCGGGACCTTCGGAGGAGGTACTGAGGCCCTGCTGCTGTGCTGGCCAG    308
      ThrTrpArgSerArgAspLeuArgArgArgGluValLeuArgProLeuLeuCysTrpArgGln

925   GGGAAGGGAGCAACAGGGCGCAGAGGTGGGAACCCTGGTACCGACTCCTGCCCCTCCGC   328
      GlyLysGlyAlaThrGlyArgGlyAsnProGlyHisArgLeuLeuProLeuArg

985   AGCTCCAGCTCCCCTGGAGAGAGGCTTGCATATGCCTACATCGCCAACATTTCTGGAGGC  348
      SerSerSerSerLeuGluArgGlyLeuHisMetProThrSerProThrPheLeuGluGly

1045  AACACAGTGGTCTGAGGGGAAATGTGAACTGATCTGTAACCAAGCCACAGAGAGCTCT    352
      AspThrValVal
```

FIG. 1B

```
1105 GTGGGGAGAGACCAGGTGACCCTCATCATGTCCCTCAGTGCCCACAGTCTGGAGGAACTGA
1165 CCACGGCTCATAGTCAGTGCCAACGGAGGCACTGACTAATCAGATTGTAGTACTGTG
1225 ACTGTGGGACCATTAAGGGTCTAGGGGGACAGCAGGCTCGAGTTTAGGGCTAGACATTT
1285 GCCACTGTACATAGGGTGTCGGCATCCTGTCTGTCCTATCTTCCAGCTTCCGGTTCC
1345 CTTCCTGCCTCCCTCTTTAAGGGCCTCCAGGCCCGGCTGGCTAGAGCTTGCTG
1405 TGCAGACCAGCGGCTGACCTGACCTCCCAGAGATAGATCAACTAACTGTCTGAGTGCT
1465 GGGATTTAAAGCCGTGTGCCCCACACACCCGCTCCTGCCACCTTCCAGAAGCAATCTTA
1525 GGCCACTTGTGAGGAAACACTCTCCCCAGAGGACCCAAGCCTTCTCTCCCTGTCTCTG
1585 AGGCCTGAATCCACAGCTCTCCCCATTTTATCAACTGCTGCTTCTCTCCCTTCCTTCTGTG
1545 TTCAGGGGAAACCACTGTGGGGGCCAGGGAGGGCTCCTGGAGTCCCAGTTTTATGCTCAG
1605 ATCTCACTGAGCACTGCTTATTGGGGAGCAGAGAGGAATCAGCTGAGGCAGTGTGGGG
1665 CAGATGTTGAGGAGAATTTGGGCTTCCTGGTGAGAAACTCTAGGGGAGGCGTTGGTTAT
1725 TCCTGGAACCCAGCCTCTCCCCACGAACTCTTCACACCCCAGCCTTGAGCTGGATGC
1785 AAAGGCTGCTTTCAATTTGTCTTTGTAGTTTTGTTTGTTGTTTTTAATT
1845 GGGACAGGATCTCACGTACCCCAGGCTGGCCTCCGACTCACTATGTAGCCAAGGCTGGCT
1905 TTGGACTTCTGACCCTCCTGCCCTCCGCTTCTGGAGTGCAGGTATTACAAGGTGTACCAC
1965 CACCACCACCACCAACAACAACAACACCTGTCTTGAAACTATCATGA
2025 ATGACAGGTTCACATAGCCTTGGGTGGCCAAGGACATCCCGGATACTCTTATGGCATCT
2085 TCCTTGAAGGACTTTGCTAAATCCTGTGAGAAGTAGAAATCCAATACGGTACAAACGG
2145 TATTTATGTGTCTGTGTATCAGTGTCTGTGACCTCCTATCCCAGTGTGGTGC
2205 TGTCTGACCTCTTATGTGCACATCCGTGTCAAGACTGCTAGAGAGATGACGGGGGTG
2265 TGTGCTTGTGGGTCTAGCCATGATCAGGCCTCCTGGGAATTGCTGAATCATCTCCC
2325 ACACACAGACACACACCTCCGCTTAAAGAAATGTGAAAGAAAGGCTGAGGAAGGG
2385 AGATTTGGAGGCAAGGAGCCAGTGCGGGAGTGTGTCTCCCCTCATACAGCTTCCAGATG
2445 TCCCCCTGTGCTGAAACCCAGAACTGGGCAATAAACAGTTCAATTTCTCTTGAAAAA
2505 AAA
```

```
                               TMD#1
         ┌─────────────────────────────────────────────────────┐
pH218  MG.......GLYSEYLNPEKVQEHYNYTKETLDMQETPSR..KVASAFIIILCCAIVENLVLIAVARN.SKFH
D2     MD....PL...NLSWYDDDLERQNWSRPFNGSEGKADRPHYNYYAMLLTLI.FI.IVFGNVLVCMAVSREKALQT
β2     MGP..P...GNDSDFLLTTNGSHV...PDHDVTEERDEAWVVGMAILMSVIVL.AIVFGNVLVITAIAKFERLQT
α2     MGSLQ.PDA.GNASWNGTEAPG...GGARATPYSLQVT...LTLVCLAGLL.MLLT.VFGNVLVIIAVFTSRALKA
5HT1A  MDVLS.PGO.GNNTTS...PPAPFETGGNTGISDVTVSYQV.ITSLLLGTLIFC.A.VLGNACVAAIALERSLQN
M1     MNTSAPPAVSPNIT.VLAPGKGPWQVA........FIGITTGLLSI.AT.VTGNLLVIISFKVNTELKT
SK     MGACV.VMTDINISSGI.......DSNATGITAFSMPGWQLALWTAAYLALVL.VA.VMGNATVIWILLAHQRMRT

TMD#2
        ┌────────────────────────────────────┐
pH218  SAMVYFLGNLAASDLIAGVA...EVANTLLSGPVTLSLT
D2     TTNYL.IVSLAVADLIVATLVMPWVVYLEVVGEWKFS..
β2     VTNYF.FITSLACADLVMGLAVVPFGASHILMKMWNFG.
α2     PQN.LFLVSLASADILVATLVIPFSLANEVMGYWYFG..
5HT1A  VANYL.IGSLAVTDLMVSVLVLPMAALYQVLNKWTLG..
M1     VNNY..FLLSLACADLIIGTFSMNLYTTYLLMGHWALG.
SK     VTNY..FIVNLALADLCMAAFNAAFNFVYASHNIWYFG.

TMD#3                                                          TMD#4
        ┌────────────────────────────────────┐                          ┌─────────────────────────────────┐
pH218  PLOWFAREGS..AFITLS..ASVFSELALAIERQVAIAKVKLNGSDKS..CRMLMLIGASWLISLIGGLPIL.GWN
D2     .RIH..CDIFVTLDVMMCTASILNLCAISIDRYTAVAMPMLVNTRYSSKRRVTVMIAIVWVLSFTISC.PLLFGLN
β2     .NFW..CEFWTSIDVLCVTASIETLCVIAVDRYIAISSPFKYQSLLTKNKAR.WILMVIVSGLTSFLPIQMHWY
α2     .KTW..CEIYLALDVLFCTSSIVHLCAISLDRYWSITQAIEYN.LKRTPRRIKAIIITVWVISAVISFPPLISIEK
5HT1A  .QVT..CDLFIALDVLCCTSSILHLCAIALDRYWAITDPIDYVNKRTPRPRALT.SLT.WLIGFLISIPPMLGWRT
M1     .TLA..CDLWLALDYASNASVMNLLLISFDRYFSVTRPLSYRAKRTPRRAALM.IGLAWLVSFVLWA.PAILFWQ
SK     .RAF..CYFQNLFPITAMFVSIYSMTATAADRYMAIVHPFQPRL.SAPGTR.AV.IAGIWLVALALAF.PQCFYST

TMD#5
        ┌──────────────────────────────┐
pH218  CLDHLEACST...VLPLYAKHYLCVVTIFSVILLAIVA
D2     NTDQNE.........CIIANPAFVVYSSIVSFYVPFIVT
β2     RATHQKA..IDCYHRETCCDFFTNQAYAIASSIVSFYVP
α2     KGGGGGPQ......PAEPRCEINDQKWYVISSCIGSFFAP
5HT1A  PEDRSDPDA........CTISKDMGYTIYSTFGAFYIP
M1     YLVGE....RTVLAGQCYIQFLSQPIIFGTAMAAFYLP
SK     ITTDEGATKCVVAWPEDSGGKMLLLYHLIVIALIYF.LP
```

FIG. 2B

```
              TMD#6
         ┌─────────────────────────────────────┐
P^H218    LYV......RIYFVVRSSHADVAGP........QTLALLKVTIVLGVFIICWLPAFSILLLDSTCPVRACPVLY
D2        LLVYIKIYIVLRKRKRVNTK-(112)-KEKKATQMLAIVLGVFIICWLPFFITHILNIHC...DCNI.P
β2        LVVMVFVYSRVFQVAKRQLQK-(33)--KEHKALKTLGIIMGIFTLCWLPFFIVNIVHVI...QDNLI.P
α2        CLIMILVVRIYQIAKRRTRV-(138)-REKRFTFVLAVIGVFVVCWFPFFFTYTLTAV....GCSV.P
5HT1A     LLLMLVLYGRIFRAARFRIPK-(111)-RERKTVKTLGIIMGTFILCWLPFFIVALVLPFCE.SSCHM.P
M1        VTVMCTLWRIYRETENRARE-(138)-KEKKAARTLSAILLAFIVTWTPYNIMVLVSTFC..KDC.P
SK        LVVMFVAVSVIGLTLWRRSVP-(13)--AKKKFVKLMVLVVTFAICWLPYHLYFILGTFQEDIYCHKFI

TMD#7
         ┌─────────────────────────────┐
          KAHY..FFAFATLNSLLNPVIYTWRSRDLRREVLRPLLC---(46)
          PVLYSAFTWLGYVNSAVNPIIYTFNIEFRKAFMKILHC
          KEVYILLNWLGYVNSAFNPLIYC.RSPDFRIAFQELL.C---(37)
          RTLFKFEFWFGYCNSSLNPVIYTIFNHDFRRAFKKIL.C---(8)
          TLLGAIINWLGYSNSLLNPVIYAYFNKDFQNAFKKIIKC---(5)
          ETLWELGYWLCYVNSTINPMCYALCNKAFRDTFRLLLC---(25)
          QQVVLALFWLAMSSTMYNPIIYCCLNHRFRSGFRLAFRC---(63)
```

```
 514  TCCCTCATCCTGTGGGCTGCCCATCATGGGCTGGAACTGCATCAGCTCGCTGTCCAGC
      SerLeuIleLeuGlyGlyLeuProIleMetGlyTrpAsnCysIleSerSerLeuSerSer  191

594  TGCTCCACCGTCTCCCGCTCTACCACAAGCACTATATTCTCTTCGCACCACCGTCTTC
      CysSerThrValLeuProLeuTyrHisLysHisTyrIleLeuPheCysThrThrValPhe  211

654  ACCCTGCTCCTGCTTCCATCGTCATCCTACTGCAGGATCTACTCCTTGGTGAGGACT
      ThrLeuLeuLeuSerIleValIleLeuTyrCysArgIleTyrSerLeuValArgThr     231

714  CGAAGCCGCCGCCTGACCTTCCGCAAGAACATCTCCAAGGCCAGCCGCCAGTTCCGAGAAG
      ArgSerArgArgLeuThrPheArgLysAsnIleSerLysAlaSerArgSerGluLys     251

774  TCTCTGGCCTTGCTGAAGACAGTGATCATTGTCCTGAGTGTCTTCATTGCCTGCTGGCC
      SerLeuAlaLeuLeuLysThrValIleIleValLeuSerValPheIleAlaCysTrpAla  271

834  CCTCTCTTCATCCTACTACTTTTAGATGTGGGGTGCAAGGCGAAGACCTGTGACATCCTG
      ProLeuPheIleLeuLeuLeuAspValGlyCysLysAlaLysThrCysAspIleLeu     291

894  TACAAAGCAGAGTACTTCCTGGTTCTGGCTGTCCTGAACTCAGGTACCAACCCCATCATC
      TyrLysAlaGluTyrPheLeuValLeuAlaValLeuAsnSerGlyThrAsnProIleIle  311

954  TACACTCTGACCAATAAGGAGATGCGCCGGGCCTTCATCAGGATCATATCTTGTTGCAAA
      TyrThrLeuThrAsnLysGluMetArgArgAlaPheIleArgIleIleSerCysCysLys  331

1114  TGCCCCAACGGAGACTCCGCTGGCAAATTCAAGAGGCCCATCCCGGGCATGGAATT
      CysProAsnGlyAspSerAlaGlyLysPheLysArgProIleIleProGlyMetGluPhe  351

1194  AGCCGCAGCAAATCAGACAACTCCTCCCACCCCAGAAGGATGATGGGACAATCCAGAG
      SerArgSerLysSerAspAsnSerSerHisProGlnLysAspAspGlyAspAsnProGlu  371

1254  ACCATTATGTCTTCTGAAACGTCAATTCTTCTTCTTAAAACCGGAAGCTGTTGATACTG
      ThrIleMetSerSerGlyAsnValAsnSerSer***                          383
```

FIG. 7B

```
1314 TTGATTCTGGCTTCATCACTCACTACCCTAGCATTTCAAAAACATCTCTCTTTCTCCACT
1374 GCTGCAAGGAAGAGCAGCCCGGAGCCTGAGAGGAGGAAGGGAGAATGTGCGGCTT
1434 GGTGATACCATGTGTAGGTAGGTTATGATTATGAACAATGCCCTGGGAAGGGTGGAGAT
1494 CAGATCTGCCTGCAGAGGGTTCCTGCCCCTAATCTCTTCACTTCCTTCCTTCAGTCGTT
1554 TCTGTTTATCCCCATACTCTTTTTTTCTCCGTTTTTCTCATTCCCCTTCTCTACC
1614 ATCGCTTTCTTTCTCTTTCTTTAAAATTTAGGGGCAACAAAAGGAATCCCACAAATGGA
1674 TATTGTGGAAAACATAGTGCTGAATGACGCAAAGAATGGTGTAAATCAAAAGATAAAT
1734 TAACTTCATAAGACTGCTATTCTCAGATGCCGTCAATGTAAAATCACCTACTTGAACATTGTAT
1794 TGGAGCAATACAGACATTTCAGACATTCACACAAAAAGCAAATACTGTAGCCTTATTTGAACAATACTGAACTCAT
1854 GCAATACATTCACACAAAAAGCAAATACTGTAGCCTTATTTGAACAATACTGAACTCAT
1914 AAATACTCATGGTTTCACTCACTGCCTCCTCTATTAAAATGTCACTCAAGAAAAGTCTTGTAACGTAAA
1974 AACACAGCGATGCCCTCCTCTATTAAAATGTCACTCAAGAAAAGTCTTGTAACGTAAA
2034 GGCAAACACATGCTAGCTACTGAGCTATGACTGTCCTTGGTCACACTCTATGGGAAAACA
2094 CCGGACTCCAC
```

FIG. 7C

5'-ccgcagacgctagccctgctcaagacggtcaccatcgtgctaggcgtc
   P  Q  T  L  A  L  L  K  T  V  T  I  V  L  G  V tttatcgtctgctggctgcccgccttcagcatcctccttctggactatgcctgtcccgtc
  F  I  V  C  W  L  P  A  F  S  I  L  L  L  D  Y  A  C  P  V cactcctgcccgatcctctacaaagcccactacttttttcgccgtctccaccctg -3'
  H  S  C  P  I  L  Y  K  A  H  Y  F  F  A  V  S  T  L

FIGURE 8

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:

-continued (A) LENGTH: 2754 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
CCCCCTCGAG CACAGCCAAC AGTCACCAAA GTCAGCCACT GGCTGTCCCG GGGCGCAGAC      60

GCCAAGGCCA CTCAGGCCAG GGCAGGGACC CTGGCCGGCC TAGCCAGTGC TCAGTCCCAT     120

GGCCCCGGCC GGCCACTGAG CCCCACCATG GGCGGTTTAT ACTCAGAGTA CCTCAATCCT     180

GAGAAGGTTC AGGAACACTA CAATTACACC AAGGAGACGC TGGACATGCA GGAGACGCCC     240

TCCCGCAAGG TGGCCTCCGC CTTCATCATC ATTTTATGCT GTGCCATCGT GGTGGAGAAC     300

CTTCTGGTGC TAATCGCAGT GGCCAGGAAC AGCAAGTTCC ACTCAGCCAT GTACCTGTTC     360

CTCGGCAACC TGGCAGCCTC CGACCTGCTG GCAGGCGTGG CCTTCGTGGC CAACACCTTG     420

CTCTCCGGAC CTGTCACCCT GTCCTTAACT CCCTTGCAGT GGTTTGCCCG AGAGGGTTCA     480

GCCTTCATCA CGCTCTCTGC CTCGGTCTTC AGCCTCCTGG CCATTGCCAT CGAGAGACAA     540

GTGGCCATCG CCAAGGTCAA GCTCTACGGC AGTGACAAAA GCTGTCGAAT GTTGATGCTC     600

ATTGGGGCCT CTTGGCTGAT ATCGCTGATT CTGGGTGGCT TGCCCATCCT GGGCTGGAAT     660

TGTCTGGACC ATCTGGAGGC TTGCTCCACT GTGCTGCCCC TCTATGCTAA GCACTATGTG     720

CTCTGCGTGG TCACCATCTT CTCTGTCATC TTACTGGCTA TCGTGGCCTT GTACGTCCGA     780

ATCTACTTCG TAGTCCGCTC AAGCCATGCG GACGTTGCTG GTCCTCAGAC GCTGGCCCTG     840

CTCAAGACAG TCACCATCGT ACTGGGTGTT TTCATCATCT GCTGGCTGCC GGCTTTTAGC     900

ATCCTTCTCT TAGACTCTAC CTGTCCCGTC CGGGCCTGTC CTGTCCTCTA CAAAGCCCAT     960

TATTTCTTTG CCTTCGCCAC CCTCAACTCT CTGCTCAACC CTGTCATCTA TACATGGCGT    1020

AGCCGGGACC TTCGGAGGGA GGTACTGAGG CCCCTGCTGT GCTGGCGGCA GGGGAAGGGA    1080

GCAACAGGGC GCAGAGGTGG GAACCCTGGT CACCGACTCC TGCCCCTCCG CAGCTCCAGC    1140

TCCCTGGAGA GAGGCTTGCA TATGCCTACA TCGCCAACAT TTCTGGAGGG CAACACAGTG    1200

GTCTGAGGGG AAATGTGAAC TGATCTGTAA CCAAGCCACA GAGAGAGCTC TGTGGGGAGA    1260

GACCAGGTGA CCTCATCATG TCCCTCAGTG CCACAGGTCT GGAGGAACTG ACCACGGCTC    1320

ATAGGTCAGG TGGCCAACGG AGGCACTGAC TAATCAGATT GTAGTACTGT GACTGTGGGG    1380

ACCATTAAGG GTCTAGGGGG ACAGCAGGCT CGAGTTTAGG GCTAGACATT TGCCACTTGG    1440

TACATAGGGT GTCGGCATCC TGTCTGTCCT ATCTTCCAGC TTCCCGGTTC CCTTCCTGCC    1500

TCCTCCTTTT AAGGGCCTCT CTACATAGCC CCGGCTGGCT AGAGCTTGCT GTGCAGACCA    1560

GGCTGACCTG GACCTCCCAG AGATAGATCA ACTAACTGTG TCCTGAGTGC TGGGATTTTA    1620

AAGCCGTGTG CCCCCACACC CGGCTCCTGC CACCTTCCAG AAGCAATCTT AGGCCACTTG    1680

TTGAGGAAAC ACTCTCCCCA GAGGACCCAA GCCTTCTTCC CTGTCTCTCT GAGGCCTGAA    1740

TCCACAGCTT CCCCATTTTA TCAACTGCTG CTTCTTCCCT TTCCTTCTGT GTTCAGGGGA    1800

AACCACTGTG GGGGCAGGGA GGGGTCCTGG GATCCCAGTT TTTATGCTCA GATCTCACTG    1860

AGCACTTGCT TTATTGGGGA GCAGAGAGGA ATCAGCTGAG GCAGTGTGGG GCAGATGTTG    1920

AGGAGAATTT GGGCTTCCTG GTGAGAAAAC TCTAGGGGAG GCGTTGGTTA TTCCTGGAAC    1980

CCAGCCTCTC TCCCCACGAA CTCTTCACAC CCGCAGCCTT GAGCTGGATG CAAAGGCTGC    2040

TTTCAATTTG TCTTTGTAGT TTTGTTTTGT TTGTTTTGT TTTTTAAAT TGGGACAGGA    2100
```

-continued

```
TCTCACGTAC CCCAGGCTGG CCTCCGACTC ACTATGTAGC CAAGGCTGGC TTTGGACTTC    2160

TGACCCTCCT GCCTCCGCTT CTGGAGTGCA GGTATTACAA GGGTGTACCA CCACCACCAC    2220

CACCACCAAC AACAACAACA ACAACAACAC CTGTCTTGAA AACTATCATG AATGACATGG    2280

TTCACATAGC CTTGGGTGGC CAAGGACATC CCGGATACTC TTATGGCATC TTCCTTGAAG    2340

GACTTTGCTA AATCCTGTGG AGAAGTAGAA AATCCAATAC GGTACAAACG GTATTTATGT    2400

GTGTCTGTGT ATCAGTGTGG GGTCTGTGAC CTCCTATCCC AGTGTGGGTG CTGTCTGACC    2460

TCTTATGTGC ACATCCGTGT CAAGACTGCT AGAGAGATGG ACGGGGGTGT GTGTGCTTGT    2520

GGGGGTCTAG CCATGATCAG GCCTCCTGGG AATTGCTGAA TCATCTCTCC CACACACAGA    2580

CACACACCTC CGCCTTAAAG AAATGTGTGA AGAAAAGGC TGAGGAAGGG GAGATTTGGG     2640

AGGCAAGGAG CCAGTCGGGA GTGTGTCTCC CCTCATACAG CTTCCCAGAT GTCCCCCTTG    2700

TGCTGGAAAC CCAGAACTGG GCCAATAAAC AGTTCAATTT CTCTTGAAAA AAAA          2754
```

(2) INFORMATION FOR SEQ ID NO:2:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Gly Gly Leu Tyr Ser Glu Tyr Leu Asn Pro Glu Lys Val Gln Glu
1               5                   10                  15

His Tyr Asn Tyr Thr Lys Glu Thr Leu Asp Met Gln Glu Thr Pro Ser
            20                  25                  30

Arg Lys Val Ala Ser Ala Phe Ile Ile Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Pro Val
                85                  90                  95

Thr Leu Ser Leu Thr Pro Leu Gln Trp Phe Ala Arg Glu Gly Ser Ala
            100                 105                 110

Phe Ile Thr Leu Ser Ala Ser Val Phe Ser Leu Leu Ala Ile Ala Ile
        115                 120                 125

Glu Arg Gln Val Ala Ile Ala Lys Val Lys Leu Tyr Gly Ser Asp Lys
    130                 135                 140

Ser Cys Arg Met Leu Met Leu Ile Gly Ala Ser Trp Leu Ile Ser Leu
145                 150                 155                 160

Ile Leu Gly Gly Leu Pro Ile Leu Gly Trp Asn Cys Leu Asp His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Val Ile Leu Leu Ala Ile Val Ala Leu
        195                 200                 205

Tyr Val Arg Ile Tyr Phe Val Val Arg Ser Ser His Ala Asp Val Ala
    210                 215                 220

Gly Pro Gln Thr Leu Ala Leu Leu Lys Thr Val Thr Ile Val Leu Gly
225                 230                 235                 240
```

-continued

```
Val Phe Ile Ile Cys Trp Leu Pro Ala Phe Ser Ile Leu Leu Leu Asp
            245                 250                 255

Ser Thr Cys Pro Val Arg Ala Cys Pro Val Leu Tyr Lys Ala His Tyr
        260                 265                 270

Phe Phe Ala Phe Ala Thr Leu Asn Ser Leu Leu Asn Pro Val Ile Tyr
        275                 280                 285

Thr Trp Arg Ser Arg Asp Leu Arg Arg Glu Val Leu Arg Pro Leu Leu
    290                 295                 300

Cys Trp Arg Gln Gly Lys Gly Ala Thr Gly Arg Arg Gly Gly Asn Pro
305                 310                 315                 320

Gly His Arg Leu Leu Pro Leu Arg Ser Ser Ser Leu Glu Arg Gly
            325                 330                 335

Leu His Met Pro Thr Ser Pro Thr Phe Leu Glu Gly Asn Thr Val Val
            340                 345                 350
```

(2) INFORMATION FOR SEQ ID NO:3:

(i) SEQUENCE CHARACTERISTICS:
        (A) LENGTH: 2232 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 269..1420

(xi) SEQUENCE DESCRIPTION: SEQ ID NO:3:

```
GAATTCTTTG CTGGTCTCCG TCAGTCGCCG ACAGCAGCAA GATGCGGATC GCGCGGTGTA      60

GACCCGGAGC CCGGCGGACG CAGCTTCGTC CCGCTTGAGC GAGGCTGCTG TTTCTCGGAG     120

GCCTCTCCAG CCAAGGAAAA ACTACATAAA AAAGCATCGG ATTGCTTGCT GACCTGGCCT     180

TGCTGTAACT GAAGGCTCGC TCAACCTCGC CCTCTAGCGT TTGTCTGGAG AAGTACCACC     240

CCGGGCTCCT GGGGACACAG TTGCGGCT ATG GTG TCC TCC ACC AGC ATC CCA       292
                                Met Val Ser Ser Thr Ser Ile Pro
                                  1               5

GTG GTT AAG GCT CTC CGC AGC CAA GTC TCC GAC TAT GGC AAC TAT GAT      340
Val Val Lys Ala Leu Arg Ser Gln Val Ser Asp Tyr Gly Asn Tyr Asp
 10                  15                  20

ATC ATA GTC CGG CAT TAC AAC TAC ACA GGC AAG CTG AAC ATC GGA GTG      388
Ile Ile Val Arg His Tyr Asn Tyr Thr Gly Lys Leu Asn Ile Gly Val
 25                  30                  35                  40

GAG AAG GAC CAT GGC ATT AAA CTG ACT TCA GTG GTG TTC ATT CTC ATC      436
Glu Lys Asp His Gly Ile Lys Leu Thr Ser Val Val Phe Ile Leu Ile
                 45                  50                  55

TGC TGC TTG ATC ATC CTA GAG AAT ATA TTT GTC TTG CTA ACT ATT TGG      484
Cys Cys Leu Ile Ile Leu Glu Asn Ile Phe Val Leu Leu Thr Ile Trp
             60                  65                  70

AAA ACC AAG AAG TTC CAC CGG CCC ATG TAC TAT TTC ATA GGC AAC CTA      532
Lys Thr Lys Lys Phe His Arg Pro Met Tyr Tyr Phe Ile Gly Asn Leu
 75                  80                  85

GCC CTC TCG GAC CTG TTA GCA GGA GTG GCT TAC ACA GCT AAC CTG CTG      580
Ala Leu Ser Asp Leu Leu Ala Gly Val Ala Tyr Thr Ala Asn Leu Leu
         90                  95                 100

TTG TCT GGG GCC ACC ACC TAC AAG CTC ACA CCT GCC CAG TGG TTT CTG      628
Leu Ser Gly Ala Thr Thr Tyr Lys Leu Thr Pro Ala Gln Trp Phe Leu
105                 110                 115                 120
```

```
CGG GAA GGA AGT ATG TTT GTG GCT CTG TCT GCC TCA GTC TTC AGC CTC      676
Arg Glu Gly Ser Met Phe Val Ala Leu Ser Ala Ser Val Phe Ser Leu
            125                 130                 135

CTT GCT ATC GCC ATT GAG CGC TAC ATC ACC ATG CTG AAG ATG AAA CTA      724
Leu Ala Ile Ala Ile Glu Arg Tyr Ile Thr Met Leu Lys Met Lys Leu
            140                 145                 150

CAC AAC GGC AGC AAC AGC TCG CGC TCC TTT CTG CTG ATC AGT GCC TGC      772
His Asn Gly Ser Asn Ser Ser Arg Ser Phe Leu Leu Ile Ser Ala Cys
            155                 160                 165

TGG GTC ATC TCC CTC ATC CTG GGT GGG CTG CCC ATC ATG GGC TGG AAC      820
Trp Val Ile Ser Leu Ile Leu Gly Gly Leu Pro Ile Met Gly Trp Asn
            170                 175                 180

TGC ATC AGC TCG CTG TCC AGC TGC TCC ACC GTG CTC CCG CTC TAC CAC      868
Cys Ile Ser Ser Leu Ser Ser Cys Ser Thr Val Leu Pro Leu Tyr His
185                 190                 195                 200

AAG CAC TAT ATT CTC TTC TGC ACC ACC GTC TTC ACC CTG CTC CTG CTT      916
Lys His Tyr Ile Leu Phe Cys Thr Thr Val Phe Thr Leu Leu Leu Leu
            205                 210                 215

TCC ATC GTC ATC CTC TAC TGC AGG ATC TAC TCC TTG GTG AGG ACT CGA      964
Ser Ile Val Ile Leu Tyr Cys Arg Ile Tyr Ser Leu Val Arg Thr Arg
            220                 225                 230

AGC CGC CGC CTG ACC TTC CGC AAG AAC ATC TCC AAG GCC AGC CGC AGT     1012
Ser Arg Arg Leu Thr Phe Arg Lys Asn Ile Ser Lys Ala Ser Arg Ser
            235                 240                 245

TCC GAG AAG TCT CTG GCC TTG CTG AAG ACA GTG ATC ATT GTC CTG AGT     1060
Ser Glu Lys Ser Leu Ala Leu Leu Lys Thr Val Ile Ile Val Leu Ser
            250                 255                 260

GTC TTC ATT GCC TGC TGG GCC CCT CTC TTC ATC CTA CTA CTT TTA GAT     1108
Val Phe Ile Ala Cys Trp Ala Pro Leu Phe Ile Leu Leu Leu Leu Asp
265                 270                 275                 280

GTG GGG TGC AAG GCG AAG ACC TGT GAC ATC CTG TAC AAA GCA GAG TAC     1156
Val Gly Cys Lys Ala Lys Thr Cys Asp Ile Leu Tyr Lys Ala Glu Tyr
            285                 290                 295

TTC CTG GTT CTG GCT GTG CTG AAC TCA GGT ACC AAC CCC ATC ATC TAC     1204
Phe Leu Val Leu Ala Val Leu Asn Ser Gly Thr Asn Pro Ile Ile Tyr
            300                 305                 310

ACT CTG ACC AAT AAG GAG ATG CGC CGG GCC TTC ATC AGG ATC ATA TCT     1252
Thr Leu Thr Asn Lys Glu Met Arg Arg Ala Phe Ile Arg Ile Ile Ser
            315                 320                 325

TGT TGC AAA TGC CCC AAC GGA GAC TCC GCT GGC AAA TTC AAG AGG CCC     1300
Cys Cys Lys Cys Pro Asn Gly Asp Ser Ala Gly Lys Phe Lys Arg Pro
330                 335                 340

ATC ATC CCG GGC ATG GAA TTT AGC CGC AGC AAA TCA GAC AAC TCC TCC     1348
Ile Ile Pro Gly Met Glu Phe Ser Arg Ser Lys Ser Asp Asn Ser Ser
345                 350                 355                 360

CAC CCC CAG AAG GAT GAT GGG GAC AAT CCA GAG ACC ATT ATG TCT TCT     1396
His Pro Gln Lys Asp Asp Gly Asp Asn Pro Glu Thr Ile Met Ser Ser
            365                 370                 375

GGA AAC GTC AAT TCT TCT TCT TAAAACCGGA AGCTGTTGAT ACTGTTGATT        1447
Gly Asn Val Asn Ser Ser Ser
            380

CTGGCTTCAT CACTCACTAC CCTAGCATTT CAAAAACATC TCTCTTTCTC CACTGCTGCA   1507

AGGAAGAAGC AGCCGGGAGC CTGAGAGAGG GAGGGAAGGG AGAATGTGCG GCTTGGTGAT   1567

ACCATGTTGT AGGTAGGTTA TGATTATGAA CAATGCCCTG GGAAGGGTGG AGATCAGATC   1627

TGCCTGCAGA GGGTTTCCTG CCCCCTCCTA ATCTCTTCAC TTCCTTCAGT CGTTTCTGTT   1687

TATCCCCCAT ACTCTTTTTT CTTTTCTCCG TTTTTCTCAT TCCCCTTCTC TACCATCGCT   1747

TTCTTTTCTC TTTCTTTAAA ATTTAGGGGC AACAAAAGGA ATCCCACAAA TGGATATTGT   1807
```

-continued

```
GGAAAACATA GTGCTGAATG ACGGCAAAGA ATGGTGGTAA ATCAAAAGAT AAATTAACTT  1867

CATAAGACTG CTATTCTGAA ATGCAACAAT CTTGTACAGT CAGGACTGAT AAAATGGAGC  1927

AATCAGACAT TTCAGATGCC CGTCAATGTA AAATCACCTA CTTGAACATT GTATGCAATA  1987

CATTCACACA AAAAAGCAAA TACTGTAGCC TTATTTGAAC AATACTGAAC TCATAAATAC  2047

TCATGGTTTC ACTCTGTCCA GGCGCCTAAG GACTATGCTG CTGTAATACA GGAAAACACA  2107

GCGGATGCCT CCTCTATTAA AATGTCACTC AAGAAAAGTC TCTTGTAACG TAAAGGCAAA  2167

CACATGTAGC TACTGAGCTA TGACTGTCCT TGGTCACACT CTATGGGAAA ACACCGGAC  2227

TCCAC                                                              2232
```

(2) INFORMATION FOR SEQ ID NO:4:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Ser Ser Thr Ser Ile Pro Val Val Lys Ala Leu Arg Ser Gln
 1               5                  10                  15

Val Ser Asp Tyr Gly Asn Tyr Asp Ile Ile Val Arg His Tyr Asn Tyr
                20                  25                  30

Thr Gly Lys Leu Asn Ile Gly Val Glu Lys Asp His Gly Ile Lys Leu
            35                  40                  45

Thr Ser Val Val Phe Ile Leu Ile Cys Cys Leu Ile Ile Leu Glu Asn
        50                  55                  60

Ile Phe Val Leu Leu Thr Ile Trp Lys Thr Lys Lys Phe His Arg Pro
65                  70                  75                  80

Met Tyr Tyr Phe Ile Gly Asn Leu Ala Leu Ser Asp Leu Leu Ala Gly
                85                  90                  95

Val Ala Tyr Thr Ala Asn Leu Leu Leu Ser Gly Ala Thr Thr Tyr Lys
               100                 105                 110

Leu Thr Pro Ala Gln Trp Phe Leu Arg Glu Gly Ser Met Phe Val Ala
           115                 120                 125

Leu Ser Ala Ser Val Phe Ser Leu Leu Ala Ile Ala Ile Glu Arg Tyr
       130                 135                 140

Ile Thr Met Leu Lys Met Lys Leu His Asn Gly Ser Asn Ser Ser Arg
145                 150                 155                 160

Ser Phe Leu Leu Ile Ser Ala Cys Trp Val Ile Ser Leu Ile Leu Gly
               165                 170                 175

Gly Leu Pro Ile Met Gly Trp Asn Cys Ile Ser Ser Leu Ser Ser Cys
           180                 185                 190

Ser Thr Val Leu Pro Leu Tyr His Lys His Tyr Ile Leu Phe Cys Thr
       195                 200                 205

Thr Val Phe Thr Leu Leu Leu Ser Ile Val Ile Leu Tyr Cys Arg
       210                 215                 220

Ile Tyr Ser Leu Val Arg Thr Arg Ser Arg Leu Thr Phe Arg Lys
225                 230                 235                 240

Asn Ile Ser Lys Ala Ser Arg Ser Ser Glu Lys Ser Leu Ala Leu Leu
               245                 250                 255

Lys Thr Val Ile Ile Val Leu Ser Val Phe Ile Ala Cys Trp Ala Pro
           260                 265                 270
```

```
Leu Phe Ile Leu Leu Leu Asp Val Gly Cys Lys Ala Lys Thr Cys
            275                 280                 285

Asp Ile Leu Tyr Lys Ala Glu Tyr Phe Leu Val Leu Ala Val Leu Asn
        290                 295                 300

Ser Gly Thr Asn Pro Ile Ile Tyr Thr Leu Thr Asn Lys Glu Met Arg
305                 310                 315                 320

Arg Ala Phe Ile Arg Ile Ser Cys Cys Lys Cys Pro Asn Gly Asp
                325                 330                 335

Ser Ala Gly Lys Phe Lys Arg Pro Ile Ile Pro Gly Met Glu Phe Ser
            340                 345                 350

Arg Ser Lys Ser Asp Asn Ser Ser His Pro Gln Lys Asp Asp Gly Asp
            355                 360                 365

Asn Pro Glu Thr Ile Met Ser Ser Gly Asn Val Asn Ser Ser Ser
            370                 375                 380
```

(2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:5:

```
Lys Glu Thr Leu Asp Met Gln Glu Thr Pro Ser Arg
1               5                   10
```

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:6:

```
Tyr Ser Glu Tyr Leu Asn Pro Glu Lys Val Gln Glu
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:7:

```
Arg Gln Gly Lys Gly Ala Thr Gly Arg Arg Gly Gly
1               5                   10
```

(2) INFORMATION FOR SEQ ID NO:8:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:8:

```
Arg Ser Ser Ser Leu Glu Arg Gly Leu His Met
 1               5                   10
```

(2) INFORMATION FOR SEQ ID NO:9:

(i) SEQUENCE CHARACTERISTICS:
        (A) LENGTH: 303 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

```
Met Asp Pro Leu Asn Leu Ser Trp Tyr Asp Asp Leu Glu Arg Gln
 1               5                   10                  15

Asn Trp Ser Arg Pro Phe Asn Gly Ser Glu Gly Lys Ala Asp Arg Pro
                20                  25                  30

His Tyr Asn Tyr Tyr Ala Met Leu Leu Thr Leu Leu Ile Phe Ile Ile
        35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
                100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
130                 135                 140

Arg Tyr Ser Ser Lys Arg Val Thr Val Met Ile Ala Ile Val Trp
145                 150                 155                 160

Val Leu Ser Phe Thr Ile Ser Cys Pro Leu Leu Phe Gly Leu Asn Asn
                165                 170                 175

Thr Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Lys Arg Lys Arg Val Asn
    210                 215                 220

Thr Lys Lys Glu Lys Lys Ala Thr Gln Met Leu Ala Ile Val Leu Gly
225                 230                 235                 240

Val Phe Ile Ile Cys Trp Leu Pro Phe Phe Ile Thr His Ile Leu Asn
                245                 250                 255

Ile His Cys Asp Cys Asn Ile Pro Pro Val Leu Tyr Ser Ala Phe Thr
            260                 265                 270

Trp Leu Gly Tyr Val Asn Ser Ala Val Asn Pro Ile Ile Tyr Thr Thr
        275                 280                 285

Phe Asn Ile Glu Phe Arg Lys Ala Phe Met Lys Ile Leu His Cys
    290                 295                 300
```

(2) INFORMATION FOR SEQ ID NO:10:

(i) SEQUENCE CHARACTERISTICS:
        (A) LENGTH: 377 amino acids
        (B) TYPE: amino acid (C) STRANDEDNESS: Not Relevant
(D) TOPOLOGY: Not Relevant (ii) MOLECULE TYPE: protein (xi) SEQUENCE DESCRIPTION: SEQ ID NO:10:

```
Met Gly Pro Pro Gly Asn Asp Ser Asp Phe Leu Leu Thr Thr Asn Gly
 1               5                  10                  15

Ser His Val Pro Asp His Asp Val Thr Glu Arg Asp Glu Ala Trp
                20                  25                  30

Val Val Gly Met Ala Ile Leu Met Ser Val Ile Val Leu Ala Ile Val
                35                  40                  45

Phe Gly Asn Val Leu Val Ile Thr Ala Ile Ala Lys Phe Glu Arg Leu
50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ser His Ile Leu Met
                85                  90                  95

Lys Met Trp Asn Phe Gly Asn Phe Trp Cys Glu Phe Trp Thr Ser Ile
                100                 105                 110

Asp Val Leu Cys Val Thr Ala Ser Ile Glu Thr Leu Cys Val Ile Ala
                115                 120                 125

Val Asp Arg Tyr Ile Ala Ile Thr Ser Pro Phe Lys Tyr Gln Ser Leu
130                 135                 140

Leu Thr Lys Asn Lys Ala Arg Met Val Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Lys Ala Ile Asp Cys Tyr His Arg Glu Thr Cys Cys Asp
                180                 185                 190

Phe Phe Thr Asn Gln Ala Tyr Ala Ile Ala Ser Ser Ile Val Ser Phe
                195                 200                 205

Tyr Val Pro Leu Val Val Met Val Phe Val Tyr Ser Arg Val Phe Gln
                210                 215                 220

Val Ala Lys Arg Gln Leu Gln Lys Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Lys Glu His Lys Ala Leu Lys
                260                 265                 270

Thr Leu Gly Ile Ile Met Gly Ile Phe Thr Leu Cys Trp Leu Pro Phe
                275                 280                 285

Phe Ile Val Asn Ile Val His Val Ile Gln Asp Asn Leu Ile Pro Lys
290                 295                 300

Glu Val Tyr Ile Leu Leu Asn Trp Leu Gly Tyr Val Asn Ser Ala Phe
305                 310                 315                 320

Asn Pro Leu Ile Tyr Cys Arg Ser Pro Asp Phe Arg Ile Ala Phe Gln
                325                 330                 335

Glu Leu Leu Cys Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa
                370                 375
```

(2) INFORMATION FOR SEQ ID NO:11:

(i) SEQUENCE CHARACTERISTICS:
        (A) LENGTH: 450 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:11:

```
Met Gly Ser Leu Gln Pro Asp Ala Gly Asn Ala Ser Trp Asn Gly Thr
 1               5                  10                  15

Glu Ala Pro Gly Gly Gly Ala Arg Ala Thr Pro Tyr Ser Leu Gln Val
                20                  25                  30

Thr Leu Thr Leu Val Cys Leu Ala Gly Leu Leu Met Leu Leu Thr Val
                35                  40                  45

Phe Gly Asn Val Leu Val Ile Ile Ala Val Phe Thr Ser Arg Ala Leu
 50                  55                  60

Lys Ala Pro Gln Asn Leu Phe Leu Val Ser Leu Ala Ser Ala Asp Ile
 65                  70                  75                  80

Leu Val Ala Thr Leu Val Ile Pro Phe Ser Leu Ala Asn Glu Val Met
                85                  90                  95

Gly Tyr Trp Tyr Phe Gly Lys Thr Trp Cys Glu Ile Tyr Leu Ala Leu
                100                 105                 110

Asp Val Leu Phe Cys Thr Ser Ser Ile Val His Leu Cys Ala Ile Ser
                115                 120                 125

Leu Asp Arg Tyr Trp Ser Ile Thr Gln Ala Ile Glu Tyr Asn Leu Lys
130                 135                 140

Arg Thr Pro Arg Arg Ile Lys Ala Ile Ile Thr Val Trp Val Ile
145                 150                 155                 160

Ser Ala Val Ile Ser Phe Pro Pro Leu Ile Ser Ile Glu Lys Lys Gly
                165                 170                 175

Gly Gly Gly Gly Pro Gln Pro Ala Glu Pro Arg Cys Glu Ile Asn Asp
                180                 185                 190

Gln Lys Trp Tyr Val Ile Ser Ser Cys Ile Gly Ser Phe Phe Ala Pro
                195                 200                 205

Cys Leu Ile Met Ile Leu Val Tyr Val Arg Ile Tyr Gln Ile Ala Lys
                210                 215                 220

Arg Arg Thr Arg Val Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
                340                 345                 350
```

-continued

```
Xaa Xaa Xaa Xaa Xaa Xaa Xaa Xaa Xaa Xaa Xaa Xaa Xaa Arg
        355                 360                 365

Glu Lys Arg Phe Thr Phe Val Leu Ala Val Val Ile Gly Val Phe Val
    370                 375                 380

Val Cys Trp Phe Pro Phe Phe Phe Thr Tyr Thr Leu Thr Ala Val Gly
385                 390                 395                 400

Cys Ser Val Pro Arg Thr Leu Phe Lys Phe Phe Trp Phe Gly Tyr
                405                 410                 415

Cys Asn Ser Ser Leu Asn Pro Val Ile Tyr Thr Ile Phe Asn His Asp
                420                 425                 430

Phe Arg Arg Ala Phe Lys Lys Ile Leu Cys Xaa Xaa Xaa Xaa Xaa
            435                 440                 445

Xaa Xaa
    450

(2) INFORMATION FOR SEQ ID NO:12:

(i) SEQUENCE CHARACTERISTICS:
        (A) LENGTH: 421 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:12:

Met Asp Val Leu Ser Pro Gly Gly Asn Asn Thr Thr Ser Pro Pro Ala
1               5                   10                  15

Pro Phe Glu Thr Gly Gly Asn Thr Thr Gly Ile Ser Asp Val Thr Val
            20                  25                  30

Ser Tyr Gln Val Ile Thr Ser Leu Leu Leu Gly Thr Leu Ile Phe Cys
        35                  40                  45

Ala Val Leu Gly Asn Ala Cys Val Val Ala Ala Ile Ala Leu Glu Arg
    50                  55                  60

Ser Leu Gln Asn Val Ala Asn Tyr Leu Ile Gly Ser Leu Ala Val Thr
65                  70                  75                  80

Asp Leu Met Val Ser Val Leu Val Leu Pro Met Ala Ala Leu Tyr Gln
                85                  90                  95

Val Leu Asn Lys Trp Thr Leu Gly Gln Val Thr Cys Asp Leu Phe Ile
            100                 105                 110

Ala Leu Asp Val Leu Cys Cys Thr Ser Ser Ile Leu His Leu Cys Ala
        115                 120                 125

Ile Ala Leu Asp Arg Tyr Trp Ala Ile Thr Asp Pro Ile Asp Tyr Val
    130                 135                 140

Asn Lys Arg Thr Pro Arg Pro Arg Ala Leu Thr Ser Leu Thr Trp Leu
145                 150                 155                 160

Ile Gly Phe Leu Ile Ser Ile Pro Pro Met Leu Gly Trp Arg Thr Pro
                165                 170                 175

Glu Asp Arg Ser Asp Pro Asp Ala Cys Thr Ile Ser Lys Asp His Gly
            180                 185                 190

Tyr Thr Ile Tyr Ser Thr Phe Gly Ala Phe Tyr Ile Pro Leu Leu Leu
        195                 200                 205

Met Leu Val Leu Tyr Gly Arg Ile Phe Arg Ala Ala Arg Phe Arg Ile
    210                 215                 220

Pro Lys Xaa Xaa Xaa Xaa Xaa Xaa Xaa Xaa Xaa Xaa Xaa Xaa Xaa
225                 230                 235                 240
```

-continued

```
Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Arg Glu Arg Lys Thr Val Lys Thr Leu Gly Ile Ile Met Gly Thr
            340                 345                 350

Phe Ile Leu Cys Trp Leu Pro Phe Phe Ile Val Ala Leu Val Leu Pro
            355                 360                 365

Phe Cys Glu Ser Ser Cys His Met Pro Thr Leu Leu Gly Ala Ile Ile
            370                 375                 380

Asn Trp Leu Gly Tyr Ser Asn Ser Leu Leu Asn Pro Val Ile Tyr Ala
385                 390                 395                 400

Tyr Phe Asn Lys Asp Phe Gln Asn Ala Phe Lys Lys Ile Ile Lys Cys
            405                 410                 415

Xaa Xaa Xaa Xaa Xaa
            420
```

(2) INFORMATION FOR SEQ ID NO:13:

(i) SEQUENCE CHARACTERISTICS:
        (A) LENGTH: 461 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

```
Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Ile Ile
            35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
            85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
            115                 120                 125

Arg Pro Leu Ser Tyr Arg Ala Lys Arg Thr Pro Arg Arg Ala Ala Leu
            130                 135                 140

Met Ile Gly Leu Ala Trp Leu Val Ser Phe Val Leu Trp Ala Pro Ala
145                 150                 155                 160
```

-continued

```
Ile Leu Phe Trp Gln Tyr Leu Val Gly Glu Arg Thr Val Leu Ala Gly
            165                 170                 175

Gln Cys Tyr Ile Gln Phe Leu Ser Gln Pro Ile Ile Thr Phe Gly Thr
            180                 185                 190

Ala Met Ala Ala Phe Tyr Leu Pro Val Thr Val Met Cys Thr Leu Tyr
            195                 200                 205

Trp Arg Ile Tyr Arg Glu Thr Glu Asn Arg Ala Arg Glu Xaa Xaa Xaa
            210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Lys Glu Lys Lys Ala Ala Arg Thr Leu
            355                 360                 365

Ser Ala Ile Leu Leu Ala Phe Ile Val Thr Trp Thr Pro Tyr Asn Ile
            370                 375                 380

Met Val Leu Val Ser Thr Phe Cys Lys Asp Cys Val Pro Glu Thr Leu
385                 390                 395                 400

Trp Glu Leu Gly Tyr Trp Leu Cys Tyr Val Asn Ser Thr Ile Asn Pro
            405                 410                 415

Met Cys Tyr Ala Leu Cys Asn Lys Ala Phe Arg Asp Thr Phe Arg Leu
            420                 425                 430

Leu Leu Leu Cys Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa
            450                 455                 460
```

(2) INFORMATION FOR SEQ ID NO:14:

(i) SEQUENCE CHARACTERISTICS:
        (A) LENGTH: 387 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:14:

```
Met Gly Ala Cys Val Val Met Thr Asp Ile Asn Ile Ser Ser Gly Leu
1               5                   10                  15

Asp Ser Asn Ala Thr Gly Ile Thr Ala Phe Ser Met Pro Gly Trp Gln
            20                  25                  30

Leu Ala Leu Trp Thr Ala Ala Tyr Leu Ala Leu Val Leu Val Ala Val
            35                  40                  45
```

```
Met Gly Asn Ala Thr Val Ile Trp Ile Ile Leu Ala His Gln Arg Met
         50                  55                  60

Arg Thr Val Thr Asn Tyr Phe Ile Val Asn Leu Ala Leu Ala Asp Leu
 65                  70                  75                  80

Cys Met Ala Ala Phe Asn Ala Ala Phe Asn Phe Val Tyr Ala Ser His
                 85                  90                  95

Asn Ile Trp Tyr Phe Gly Arg Ala Phe Cys Tyr Phe Gln Asn Leu Phe
                100                 105                 110

Pro Ile Thr Ala Met Phe Val Ser Ile Tyr Ser Met Thr Ala Ile Ala
                115                 120                 125

Ala Asp Arg Tyr Met Ala Ile Val His Pro Phe Gln Pro Arg Leu Ser
130                 135                 140

Ala Pro Gly Thr Arg Ala Val Ile Ala Gly Ile Trp Leu Val Ala Leu
145                 150                 155                 160

Ala Leu Ala Phe Pro Gln Cys Phe Tyr Ser Thr Ile Thr Thr Asp Glu
                165                 170                 175

Gly Ala Thr Lys Cys Val Val Ala Trp Pro Glu Asp Ser Gly Gly Lys
                180                 185                 190

Met Leu Leu Leu Tyr His Leu Ile Val Ile Ala Leu Ile Tyr Phe Leu
                195                 200                 205

Pro Leu Val Val Met Phe Val Ala Tyr Ser Val Ile Gly Leu Thr Leu
210                 215                 220

Trp Arg Arg Ser Val Pro Xaa Xaa Xaa Xaa Xaa Xaa Xaa Xaa Xaa Xaa
225                 230                 235                 240

Xaa Xaa Xaa Ala Lys Lys Phe Val Lys Thr Met Val Leu Val Val Val
                245                 250                 255

Val Thr Phe Ala Ile Cys Trp Leu Pro Tyr His Leu Tyr Phe Ile Leu
                260                 265                 270

Gly Thr Phe Gln Glu Asp Ile Tyr Cys His Lys Phe Ile Gln Gln Val
                275                 280                 285

Tyr Leu Ala Leu Phe Trp Leu Ala Met Ser Ser Thr Met Tyr Asn Pro
290                 295                 300

Ile Ile Tyr Cys Cys Leu Asn His Arg Phe Arg Ser Gly Phe Arg Leu
305                 310                 315                 320

Ala Phe Arg Cys Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa Xaa Xaa
                370                 375                 380

Xaa Xaa Xaa
385
```

(2) INFORMATION FOR SEQ ID NO:15:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CCGCAGACGC TAGCCCTGCT CAAGACGGTC ACCATCGTGC TAGGCGTCTT TATCGTCTGC      60

TGGCTGCCCG CCTTCAGCAT CCTCCTTCTG GACTATGCCT GTCCCGTCCA CTCCTGCCCG     120

ATCCTCTACA AAGCCCACTA CTTTTTCGCC GTCTCCACCC TG                       162
```

(2) INFORMATION FOR SEQ ID NO:16:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Pro Gln Thr Leu Ala Leu Leu Lys Thr Val Thr Ile Val Leu Gly Val
                  5                  10                  15
Phe Ile Val Cys Trp Leu Pro Ala Phe Ser Ile Leu Leu Leu Asp Tyr
             20                  25                  30
Ala Cys Pro Val His Ser Cys Pro Ile Leu Tyr Lys Ala His Tyr Phe
         35                  40                  45
Phe Ala Val Ser Thr Leu
     50
```

MOLECULAR CLONING AND EXPRESSION OF G-PROTEIN COUPLED RECEPTORS

CROSS-REFERENCE TO A RELATED APPLICATION

This application is a continuation-in-part of application Ser. No. 08/760,936, filed on Dec. 6, 1996, now U.S. Pat. No. 5,856,443, which is a continuation of application Ser. No. 08/196,989, filed on Feb. 15, 1994, now U.S. Pat. No. 5,585,476.

This invention was made with government support under the National Institute on Drug Abuse grant number DA07244. The government has certain rights in this invention.

BACKGROUND OF THE INVENTION

The development of multicellular organisms requires the orchestration of many precisely coordinated events involving cell-type specific growth, proliferation, differentiation, migration, and cell death. Not surprisingly, intercellular communication plays critical roles in these processes. Although the molecular mechanisms involved in this communication are in general poorly understood, this research field is characterized by increasingly rapid progress initiated by the realization that viral oncogenes are, in many cases, transformed versions of cellular genes (proto-oncogenes) that participate in the intercellular communication directing development. Furthermore, it has been established that many non-viral forms of cancer also result from transformation of genes involved in signal transduction (e.g. growth factors, growth factor receptors, and transcription factors).

A large number of mammalian growth factor receptors have been cloned and many are recognized proto-oncogenes (Yarden and Ullrich, 1988). Most of these cloned receptors are members of a superfamily of integral membrane proteins with intrinsic, growth factor-inducible, tyrosine kinase activity. An extensive research literature now documents the critical roles these receptors play in cell proliferation, differentiation, and malignant transformation. However, multiple lines of evidence suggest that members of the G-protein coupled receptor (GPR) superfamily may also participate in mammalian development and oncogenesis. For example, both the yeast *S. cerevisiae* and the slime mold *D. discoideum* express GPRs that regulate cell differentiation (Devreotes, 1989; Sprague, 1991). In addition, mammalian mitogenesis and cell proliferation are affected by several peptides and neurotransmitters which are known to interact with GPRs (Hanley, 1989; Zachary et al., 1987).

Perhaps the most direct evidence linking GPRs with ontogeny and cancer has been provided by the ectopic expression of GPRs in tissue culture cells. Thus, the mas oncogene encodes a putative GPR ($p^{mas}$) and leads to malignant transformation when transfected into NIH3T3 mouse fibroblasts cells (Young et al., 1986). In addition, several serotonin and muscarinic acetylcholine receptors (all GPRs) also produce this malignant transformation if ectopically expressed in NIH3T3 cells and stimulated by their respective ligands (Gutkind et al., 1991; Julius et al., 1989; Julius et al., 1990). While these data illustrate that GPRs can greatly influence cell proliferation and morphology, the GPRs that were studied are unlikely to be involved in these processes in vivo because they reside in fully differentiated, postmitotic cells such as neurons where serotonergic receptors, muscarinic receptors, and most likely $p^{mas}$ regulate the changing electrical properties of neuronal membranes involved in neurotransmission. However, these data support the possibility that other GPRs are expressed in vivo in immature cells where they regulate proliferation and differentiation. Furthermore, these data suggest that some forms of cancer may result from mutations or viral infections that lead to improper functioning, activation, or expression of such GPRS. Thus, identification and characterization of such receptors should significantly advance both the study of normal development as well as the search for diagnostic and therapeutic tools in oncology.

BRIEF SUMMARY OF THE INVENTION

The subject invention concerns the cloning and sequencing of cDNAs and the proteins encoded by those cDNAs. The cDNAs encode novel polypeptides that are members of the G-protein coupled receptor (GPR) superfamily. The proteins encoded by the DNAs of the subject invention are involved in the regulation of cell proliferation and/or differentiation in vivo. The subject protein receptors are endogenously expressed in various tissues and cell lines.

Specifically, the subject invention concerns the cloning and sequencing of a rat cDNA (H218) that encodes a novel GPR designated $p^{H218}$. Further included in the subject invention are mammalian homologs, including the human homolog of the H218 cDNA. The H218 cDNA was used to determine that H218 mRNA is expressed in all developing organs tested and in seven out of seven cell lines tested. In addition, in the brain, H218 mRNA is much more highly expressed during a period of extensive proliferation and differentiation (embryogenesis) than a period of very limited cell proliferation and differentiation (adulthood), suggesting that $p^{H218}$ does not function as a neurotransmitter receptor. Rather, $p^{H218}$ functions as a growth factor ligand receptor.

The subject invention further concerns antibodies from animals immunized with peptides derived from $p^{H218}$ GPR. Purified antibody made against one of the peptides recognizes a protein having an apparent molecular weight of 50–55 kDA as determined by Western blot analysis.

The subject invention also concerns cDNA of the rat-edg gene. Rat-edg cDNA encodes a GPR, $p^{rat-edg}$. The $p^{rat-edg}$ can be activated by some of the same ligand(s) that activate $p^{H218}$. By identifying compounds that specifically activate or inhibit this class of receptors one can develop unique, pharmaceutical therapies that effectively treat some forms of cancer.

A further aspect of the subject invention concerns polynucleotide molecules that are antisense to mRNA of H218 and rat-edg. The antisense polynucleotide molecules can be used to reduce or inhibit the expression of the subject protein by binding to the complementary mRNA transcripts.

The subject invention also concerns methods of use for the polynucleotide sequences, the encoded proteins, peptide fragments thereof, polynucleotide molecules that are antisense to the H218 and rat-edg sequences, and antibodies that bind to the proteins and peptides. Such use includes diagnostic and therapeutic applications of the subject invention.

BRIEF DESCRIPTION OF THE DRAWINGS

FIGS. 1A–1C shows the nucleotide (SEQ ID NO.1) and deduced amino acid sequence (SEQ ID NO.2) of H218 cDNA. The sequence was compiled from that of "H2" cDNA (nucleotides 16 to 2505) and "18" cDNA (nucleotides-155 to 288) which are identical throughout the region of overlap. A black box highlights the optimal consensus sequence for translation initiation. A potential polyadenylation signal is double-underlined and a consensus sequence associated with mRNA instability is boxed. Repetitive nucleic acid sequences in the 3Q untranslated region are underlined. An arrow designates a predicted N-glycosylation site. A consensus sequence for proline directed kinases is underlined with a broken line. Brackets below the amino acid sequence indicate possible nucleotide binding site components in the carboxy-terminal and "third cytoplasmic loop" domains respectively.

FIGS. 2A and 2B shows a comparison of $p^{H218}$ (SEQ ID NO.2) with other G-protein coupled receptors. Black boxes highlight residues identical to $p^{H218}$ residues. D2=D2 dopaminergic receptor (SEQ ID NO.9); β2=β2 adrenergic receptor (SEQ ID NO.10); α2=α2 adrenergic receptor (SEQ ID NO.11); 5HT1A=1A serotonergic receptor (SEQ ID NO.12.); M1=M1 muscarinic receptor (SEQ ID NO.13); SK=substance K receptor (SEQ ID NO.14). The numbers in parentheses indicate the number of omitted residues.

FIGS. 7A–7C shows the nucleotide (SEQ ID NO.3) and deduced amino acid sequence (SEQ ID NO.4) of rat-edg cDNA. An ATTTA motif is boxed in black.

FIG. 8 shows a partial nucleotide sequence (SEQ ID NO.15) of a cDNA that encodes a human $p^{H218}$ polypeptide (SEQ ID NO.16).

BRIEF DESCRIPTION OF THE SEQUENCES

Figure 3A:
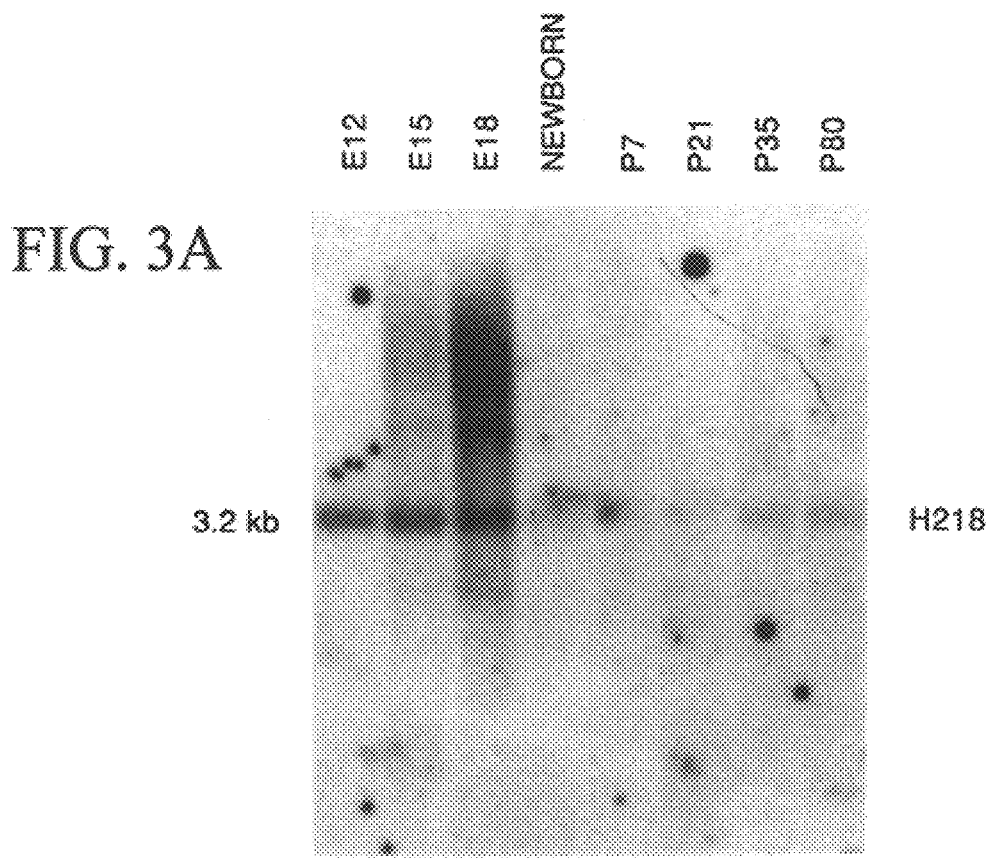
FIGS. 3A and 3B shows an X-ray autoradiograph of a Northern blot illustrating the ontogenic regulation of H218 mRNA levels in the rat brain: Poly-A RNA was extracted from whole rat brain at embryonic days 12, 15, 18, Birth, postnatal days 7, 21, 35, and 80 (adult). The resulting blot was probed for H218 mRNA (panel A), stripped, and then probed with a cyclophilin cDNA (panel B) to control for variation in extraction, loading, and transfer (brain cyclophilin mRNA levels are reported to be stable from E12 to adult). The relative intensity of the cyclophilin bands have consistently paralleled results obtained from probing the same blots with an oligo-dT probe designed to hybridize to all mRNA poly-A tails.

SEQ ID NO. 1 is the nucleotide sequence of the $^{H218}$ cDNA.

SEQ ID NO. 2 is the deduced amino acid sequence of the $p^{H218}$ protein encoded by the H218 cDNA.

SEQ ID NO. 3 is the nucleotide sequence of the rat-edg cDNA.

SEQ ID NO. 4 is the deduced amino acid sequence of the $p^{rat-edg}$ protein encoded by the rat-edg cDNA.

SEQ ID NO. 5 is the amino acid sequence of a synthetic $p^{H218}$ peptide designated peptide 1.

SEQ ID NO. 6 is the amino acid sequence of a synthetic $p^{H218}$ peptide designated peptide 2.

SEQ ID NO. 7 is the amino acid sequence of a synthetic $p^{H218}$ peptide designated peptide 3.

SEQ ID NO. 8 is the amino acid sequence of a synthetic $p^{H218}$ peptide designated peptide 4.

SEQ ID NO. 9 is the amino acid sequence of a D2 dopaminergic receptor.

SEQ ID NO. 10 is the amino acid sequence of a β2 adrenergic receptor.

SEQ ID NO. 11 is the amino acid sequence of a α2 adrenergic receptor.

SEQ ID NO. 12 is the amino acid sequence of a 1A serotonergic receptor.

SEQ ID NO. 13 is the amino acid sequence of a M1 muscarinic receptor.

SEQ ID NO. 14 is the amino acid sequence of a substance K receptor.

SEQ ID NO. 15 is a partial nucleotide sequence encoding a human $p^{H218}$ polypeptide.

SEQ ID NO. 16 is an amino acid sequence of a human $p^{H218}$ polypeptide encoded by SEQ ID NO. 15.

DETAILED DISCLOSURE OF THE INVENTION

The subject invention concerns novel cDNAs (H218 and rat-edg) that encode G-protein coupled receptors. The proteins, designated $p^{H218}$ and $p^{rat-edg}$, play important roles in cell proliferation and differentiation, and in disease states such as cancer.

It has been determined that the protein encoded by H218 polynucleotides is a receptor for sphingosine-1-phosphate (S1P). The research literature indicates that S1P can affect cellular processes potentially involved in many functions including nervous system development, nervous system responses to injury, tumorogenesis, metastasis, inflammation and heart function (Bunemann et al., 1996; Postma et al., 1996; van Koppen et al., 1996; Kawa et al., 1997; Yamamura et al., 1997). Therefore, agonists and antagonists for H218 may be of great clinical value in the treatment of disorders related to the above listed functions, and potentially other, as yet to be discovered, functions.

Rat H218 cDNA has been completely sequenced (SEQ ID NO. 1) and the amino acid sequence of the polypeptide that it encodes determined (SEQ ID NO. 2) (FIG. 1). The H218 cDNA contains a 1056 bp open reading frame that encodes a polypeptide of 352 amino acids. The 3Q untranslated region of H218 cDNA contains repetitive sequences, a consensus sequence for mRNA instability, and a series of terminal adenosines preceded by a potential polyadenylation site. The predicted cytoplasmic regions of $p^{H218}$ contain potential nucleotide binding site components and a consensus sequence for proline directed kinases involved in cell division and growth factor responses.

Analysis of the deduced amino acid sequence of $p^{H218}$ revealed that it is a member of the GPR superfamily (FIG. 2). Several features of $p^{H218}$ are common to all other GPRs, including: 1) seven regions of hydrophobicity which are predicted to act as membrane spanning domains, 2) a consensus sequence for N-linked glycosylation in its predicted N-terminal extracellular domain, and 3) a conserved cysteine residue and several serine and threonine residues in its predicted intracellular C-terminal domain. In addition, $p^{H218}$ contains many other residues which are highly conserved among most GPRs. However, $p^{H218}$ is distinct from these GPRs in that it does not contain certain highly conserved residues. Perhaps most notable are the aspartate and tyrosine residues at the cytoplasmic end of the third transmembrane domain, and the cysteine residue at the extracellular end of the same transmembrane domain.

$p^{H218}$ affects the course of cellular proliferation and/or differentiation events. Of all cloned proteins, $p^{H218}$ is most homologous to human $p^{edg}$, a putative GPR implicated in endothelial cell differentiation. The possibility of a direct interaction between $p^{H218}$ and growth-related intracellular proteins is suggested by the similarity between the predicted cytoplasmic region of $p^{H218}$ and motifs of the src homology domain 2 (SH2) found in many cytoplasmic proteins that are critically involved in growth-related signal transduction, including several proteins encoded by oncogenes.

A further aspect of the subject invention concerns polynucleotide molecules which encode the human homolog of the rat H218 gene. Human cDNAs that hybridize with rat H218 cDNA were isolated from a human embryonic brain cDNA library. A cDNA sequence (SEQ ID NO.15) encoding part of the human H218 protein (SEQ ID NO.16) is shown in FIG. 8. Also contemplated within the scope of the present invention are human genomic H218 polynucleotide sequences, including polynucleotide sequences that flank the protein coding region. These sequences include regulatory sequences and intron sequences.

The human H218 protein is also contemplated within the scope of the invention. In one embodiment, the human H218 protein comprises the amino acid sequence shown in FIG. 8. Fragments and variants of the human H218 protein, including those that are biologically active or that are capable of ligand binding, are also within the scope of the invention.

The subject invention also concerns methods for screening for and identifying ligands of the H218 proteins of the invention. The H218 polynucleotides of the invention can be used to express the H218 protein in any of a wide variety of different expression systems. The H218 protein can then be used to identify H218 agonists and H218 antagonists. The agonists and antagonists can be identified based on their ability to bind to the H218 protein. For example, polynucleotides encoding H218 can be introduced into procaryotic or eucaryotic cells, thereby causing the cells to make H218 protein from the H218 polynucleotides. Therefore, these cells express more H218 protein than they would if the H218 polynucleotides had not been introduced into them. Consequently, H218 ligands can be identified by screening compounds for their ability to bind more to the cells that express greater levels of H218 protein. The ligands may be labeled with radioactive isotopes, or chemical modifications. Alternatively, umnodified ligands may be tracked with other approaches such as antibody recognition. In addition, ligands can also be identified based on their ability to activate H218 protein. When identifying H218 ligands based on their ability to activate H218, activation of H218 can be measured using any of a number of different methods known in the art. For example, one can measure changes in 1) H218-induced intracellular signal transduction events, 2) H218 conformation, 3) proteins bound to H218, and 4) H218-induced changes in cell behavior or morphology.

Ligands identified using the above methods are also within the scope of the invention.

H218-related nucleic acids can also be used to reduce expression of H218 protein in cells. The ability of ligands to bind to H218 protein or to activate H218, as discussed above, can then be used to identify H218 ligands by comparing cells which express native concentrations of H218 with cells in which H218 concentrations have been reduced. Methods to reduce H218 protein concentrations in cells include, for example, antisense techniques and homologous recombination techniques.

The subject invention also concerns H218-specific nucleic acid probes which can be used to identify mutations in the H218 gene. Identifying such mutations may be important in the scientific study of those diseases which involve mutations in the H218 gene. In addition, identifying the mutations may contribute to the clinical diagnosis, management and counseling related to these diseases. Similarly, antibodies raised against H218 protein sequence may be useful in identifying disease-related changes in H218 protein. The scientific and clinical uses of such antibodies would be the same as those outlined above for the H218-specific nucleic acid probes.

The subject invention also concerns methods for providing gene therapy to a patient in need of such therapy by introducing into the cells of the patient, by in vivo or ex vivo means, a polynucleotide vector that can increase or decrease H218 expression. A polynucleotide expression vector comprising a polynucleotide of the invention that encodes an H218 protein can be used to increase levels of H218 expression in cells. In one embodiment, the polynucleotide encodes the human H218 protein which comprises the amino acid sequence shown in FIG. 8 (seq id no.16). Similarly, H218 protein levels can be decreased in cells using, for example, antisense sequences or homologous recombination techniques. Methods of providing gene therapy are known in the art.

A further aspect of the subject invention concerns antibodies raised against synthetic peptides of $p^{H218}$. These peptides, designated as 1, 2, 3, and 4 (and corresponding to SEQ ID NO. 5, SEQ ID NO. 6, SEQ ID NO. 7, and SEQ ID NO. 8, respectively), correspond to separate extracellular and intracellular regions of $p^{H218}$. These peptides and their amino acid sequence are shown in Table 1.

TABLE 1

Amino Acid Sequences of $p^{H218}$ peptides

| $p^{H218}$ peptide | | Sequence |
| --- | --- | --- |
| peptide 1 | SEQ ID NO. 5 | KETLDMQETPSR |
| peptide 2 | SEQ ID NO. 6 | YSEYLNPEKVQE |
| peptide 3 | SEQ ID NO. 7 | RQGKGATGRRGG |
| peptide 4 | SEQ ID NO. 8 | RSSSSLERGLHM |

Polyclonal antibodies that react with the antigen peptides were raised in rabbits immunized with the respective peptide. Each antibody recognizes by an ELISA assay the specific peptide used as the immunogen. One of the antibodies, from a rabbit immunized with peptide 1 (SEQ ID NO. 5), was affinity purified and.used in a Western blot with antigens from a cell line that expresses H218 mRNA. This antibody recognized a band of 50 to 55 kDa, and a band of 180 to 200 kDa in the Western blot. These antibodies can be used for detecting and purifying the $p^{H218}$ protein through standard procedures known in the art. The antibodies can also be used for localization of $p^{H218}$ in tissues using immunohistochemical techniques known in the art.

The subject invention further contemplates the use of the protein and peptides to generate both polyclonal and monoclonal antibodies. Contemplated within the scope of the invention are antibodies to wild type forms of H218, as well as mutated forms of H218 protein. Monoclonal antibodies to $p^{H218}$, and peptide fragments thereof, can be produced using the teachings provided herein in combination with procedures that are well known in the art. Such antibodies can be produced in several host systems, including mouse, rat, and human. In one embodiment, the antibodies of the invention bind to human H218 protein.

Also included within the scope of the invention are binding fragments of the antibodies of the subject invention. Fab', F(ab')$_2$, and Fv fragments may be obtained by conventional techniques, such as proteolytic digestion of the antibodies by papain or pepsin, or through standard genetic engineering techniques using polynucleotide sequences that encode binding fragments of the antibodies of the subject invention.

A further aspect of the subject invention concerns the cloning and sequencing of the rat homolog of the human edg gene, which also encodes a GPR. This rat gene, designated rat-edg, is similar in sequence to the human edg gene. The rat-edg cDNA (SEQ ID NO. 3) encodes a protein, $p^{rat-edg}$ (SEQ ID NO. 4). The $p^{rat-edg}$ protein also has several features in common with other members of the GPR superfamily including 1) seven hydrophobic regions presumed to act as transmembrane domains, 2) a putative N-glycosylation site in the N-terminal domain, 3) putative phosphorylation sites in cytoplasmic domains, and 4) a conserved cysteine residue in the C-terminal domain.

The subject invention also concerns polynucleotide molecules having sequences that are antisense to mRNA transcripts of H218 and rat-edg polynucleotides. An administration of an antisense polynucleotide molecule can block the production of the protein encoded by H218 or rat-edg. The techniques for preparing antisense polynucleotide molecules, and administering such molecules are known in the art. For example, antisense polynucleotide molecules can be encapsulated into liposomes for fusion with cells.

As is well known in the art, the genetic code is redundant in that certain amino acids are coded for by more than one nucleotide triplet (codon). The subject invention includes those polynucleotide sequences which encode the same amino acids using a different codon from that specifically exemplified in the sequences herein. Such a polynucleotide sequence is referred to herein as an "equivalent" polynucleotide sequence. Thus, the scope of the subject invention includes not only the specific polynucleotide sequences depicted herein, but also all equivalent polynucleotide sequences encoding the polypeptides of the subject invention, and fragments or variants thereof.

The polynucleotide sequences of the subject invention can be prepared according to the teachings contained herein, or by synthesis of oligonucleotide fragments, for example by using a "gene machine" using procedures well known in the art.

The polypeptides of the subject invention can be prepared by expression of the cDNAs in a compatible host cell using an expression vector containing the polynucleotide sequences of the subject invention. The polypeptides can then be purified from the host cell using standard purification techniques that are well known in the art. Alternatively, the polypeptides of the subject invention can be chemically synthesized using solid phase peptide synthesis techniques known in the art.

The polypeptides of the subject invention can be used as molecular weight markers, as an immunogen for generating antibodies, and as an inert protein in certain assays. The polynucleotide molecules of the subject invention can be used as DNA molecular weight markers, as a chromosome marker, and as a marker for the gene on the chromosome.

The term "polynucleotide sequences" when used in reference to the subject invention can include all or a portion of the cDNA. Similarly, polynucleotide sequences of the subject invention also includes variants, including allelic variations or polymorphisms of the genes. The polynucleotide sequences of the invention may be composed of either RNA or DNA. More preferably, the polynucleotide sequences of the subject invention are composed of DNA.

As used herein, the term "isolated" means, in the case of polynucleotide sequences, that the sequence is no longer linked or associated with other polynucleotide sequences with which it would naturally occur. Thus, the claimed polynucleotide sequences can be inserted into a plasmid or other vector, to form a recombinant DNA cloning vector. The cloning vector may be of bacterial or viral origin. The vector may be designed for the expression of the polypeptide encoded by the polynucleotide sequence. The vector may be transformed or transfected or otherwise inserted into a host cell. The host cell may be either prokaryotic or eukaryotic, and would include bacteria, yeast, insect cells, and mammalian cells. For example, a bacterial host cell may be $E.$ $coli,$ and a mammalian host cell may be the PC12 cell line.

As used herein, the term "isolated" means, in the case of proteins, obtaining the protein in a form other than that which occurs in nature. This may be, for example, obtaining $p^{H218}$ by purifying and recovering the protein from a host cell transformed to express the recombinant protein. In the case of antibodies, "isolated" refers to antibodies, which, through the hand of man, have been produced or removed from their natural setting. Thus, isolated antibodies of the subject invention would include antibodies raised as the result of purposeful administration of the proteins, or peptide fragments thereof, of the subject invention in an appropriate host.

The various genetic engineering methods employed herein are well known in the art, and are described in Sambrook, J., et al. (1989) *Molecular Cloning: A Laboratory Manual,* Cold Spring Harbor Laboratory, New York. Thus, it is within the skill of those in the genetic engineering art to screen cDNA libraries, perform restriction enzyme digestions, electrophorese DNA fragments, tail and anneal vector and insert DNA, ligate DNA, transform or transfect host cells, prepare vector DNA, electrophorese proteins, sequence DNA, perform Northern, Southern and Western blotting, and perform PCR techniques.

Materials and Methods

Cloning of H218 cDNA. A "LAMBDA ZAP" cDNA library (Stratagene, La Jolla, Calif.) constructed using rat hippocampal RNA was screened at medium stringency with a 926 bp 5Q EcoRI-Bgl II 3Q fragment of a D2 dopamine receptor cDNA (MacLennan et al., 1990). The cDNA was labeled with $^{32}P$ by random hexamer priming. Nitrocellulose filters were incubated for 2 hrs at 42° C. in 5×SSPE (1×SSPE=0.15 M NaCl, 12 mM NaH$_2$PO$_4$H2O, 1 mM EDTA, pH 7.4), 40% formamide, 0.15% SDS, 5×Denhardt's solution, 100 μg/ml denatured salmon sperm DNA, and 2 μg/ml polyadenylic acid. The filters were then incubated overnight in the same solution at 42° C. with the probe added (approximately 10$^6$ cpm/ml). The filters were washed two times for 15 minutes each at room temperature in 2×SSC (standard saline citrate buffer: 1×SSC=0.15 M NaCl, 0.015 M sodium citrate, pH 7.2), followed by two washes for 45 minutes each at 42° C. in 2×SSC.

In order to exclude D2 receptor cDNAs from analysis, all hybridizing phage were screened at high stringency with four oligodeoxynucleotide probes designed to specifically recognize D2 dopamine receptor cDNAs (MacLennan et al., 1990). All phage that hybridized to the oligonucleotides were eliminated from further rounds of purification. All other phage that hybridized to the cDNA probe were purified, converted into "BLUESCRIPT" plasmids (Stratagene) according to the manufacturer's automatic excision protocol, and evaluated by restriction digests and gel electrophoresis. Sequence analysis revealed that one of the hybridizing cDNAs, designated "H2", encodes a portion of a putative G-protein coupled receptor (GPR), based on sequence comparisons to other GPRs.

A modified polymerase chain reaction (PCR) technique was used to clone the 5Q cDNA for the H218 cDNA (Loh et al., 1989). H2 cDNA extends 2.6 kb to a 5' end that encodes part of the presumed extracellular N-terminal domain of the receptor. Thus, an oligodeoxynucleotide corresponding to the antisense strand of H2 (nucleotides 288 to 312 of H218) primed the first strand cDNA synthesis with M-MLV Reverse Transcriptase (Gibco-BRL, Gaithersburg, Md.). Poly-A RNA extracted from postnatal day 14 (P14) rat lung served as a template. Terminal Deoxynucleotidyl Transferase (Gibco-BRL) was used to "tail" the resulting cDNA with guanines. The cDNA was then subjected to 35 rounds of PCR amplification with "AMPLITAQ" DNA polymerase (Perkin-Elmer, Branchburg, N.J.) The reaction was primed with an internal H2 specific primer containing antisense strand nucleotides 263 to 288 of H218 and a primer containing a poly-cytosine sequence. The resulting "18"cDNA was subcloned into a "BLUESCRIPT" plasmid (Stratagene) by exploiting restriction sites designed into the 5' ends of the PCR primers.

The "H2" and "18" cDNA fragments were then spliced together to form a 2.75 kb cDNA (designated "H218") containing a complete open reading frame (ORF) of 1052 bp that encodes a polypeptide of 352 amino acids.

Characterization of cDNA Clones The nucleotide sequences of both strands of the H218 cDNA were determined by the dideoxy chain termination technique (Sanger et al., 1977). The T7 Sequencing kit (Pharmacia, Piscataway, N.J.) was used with denatured, double-stranded cDNAs in "BLUESCRIPT" plasmids serving as templates.

Tissue Preparation For RNA preparations, Long Evans rats were killed by decapitation and their brains were immediately removed and dissected. Individual brain regions were frozen in liquid nitrogen. Rats and embryos of both sexes were used in the developmental study. Brains taken from embryos are designated with an "E" and those taken postnatally are designated with a "P". For example, a brain removed 20 days after birth would be P20.

RNA Preparation, Electrophoresis, and Blotting Frozen, dissected brain regions were pooled. The "FASTTRACK" kit (Invitrogen Corp., San Diego, Calif.) was used to extract Poly-A RNA from tissue culture cells and brain tissue used in the developmental study. Total RNA was extracted by homogenization in 4 M guanidine thiocyanate followed by centrifugation through 5.7 M CsCl according to the method of Chirgwin (Chirgwin et al., 1979). The RNA was purified by repeated ethanol precipitations, and its concentration was estimated spectrophotometrically from $A_{260}$. All RNA samples were stored at −20° C. as ethanol precipitates.

RNA (1–10 μg of Poly-A or 20 μg of total) was denatured in 50% deionized formamide, 6.0% formaldehyde at 65° C. for 5 min and then size-fractionated by electrophoresis on a horizontal agarose gel (1.25%) containing 6.0% formaldehyde. The RNA was subsequently transferred to nylon membranes (ICN BIOTRANS membrane), which were then dried and baked at 80° C. for 2 hours under vacuum. Membranes were prehybridized for 2 hrs at 42° C. in 5×SSC, 50% formamide, 0.5% SDS, 50 mM sodium phosphate (pH 6.5) containing 250 μg/ml denatured salmon sperm DNA, 5×Denhardt's solution, and 100 μg/ml polyadenylic acid. The H2 cDNA probe was then $^{32}$P-labeled by random hexamer priming, and added to the prehybridization solution. After hybridization at 42° C. overnight, the membranes were washed twice for 30 min at room temperature in 2×SSC and twice for 45 min at 60° C. in 0.1×SSC, 0.1% SDS.

Membranes were exposed to X-ray film with two intensifying screens at −80° C. for several different time intervals in order to ensure that all comparisons were made within the linear sensitivity range of the film. The probe was then removed from the membranes by washing at 65° C. in 50% formamide, 10 mM sodium phosphate, pH 6.5%, for 1 hour. Stripped blots were rinsed in 2×SSC, 0.1% SDS and exposed to film to check for complete removal of probe. To correct for possible intersample variability in extraction, loading, or transfer of the RNA, the membranes were probed with $^{32}$P-labeled rat cDNA that recognizes ribosomal RNA or with a rat cyclophilin cDNA. Brain Gyclophilin mRNA levels are reported to be stable during brain development (Danielson et al., 1988).

Tissue Culture Cells were grown on plates in Dulbecco's Modified Eagle Media (DMEM) containing 10% fetal bovine serum (FBS), with the exception of PC12 cells which were grown in RPMI media containing 10% horse serum and 5% FBS. Tissue culture cells were washed with 1×PBS, pH 7.4 while anchored to plates, mechanically dislodged, and collected by centrifugation for RNA extraction.

Antibody Production Four peptides having amino acid sequences based on the deduced sequence of $p^{H218}$, and that correspond to separate extracellular and intracellular regions of $p^{H218}$ were synthesized by the Interdisciplinary Center for Biotechnology Research Core lab at the University of Florida. Rabbits were immunized with the peptides and antiserum prepared according to standard methods. Antisera (designated "1A") from the rabbit immunized with peptide 1 (SEQ ID NO. 5) was purified by precipitation with 4.1 M saturated ammonium sulfate at 25° C. overnight. The precipitate was dissolved in PBS and dialyzed against several changes of PBS. The 0.1A antibody was then affinity purified over a CNBr-Sepharose affinity column (Sigma Chemical, St. Louis, Mo.) to which the peptide 1 (SEQ ID NO. 5) had been attached. Antibody was eluted with 0.1M glycine, pH 2.5.

Western Blotting Crude cellular protein extract or membrane preparations from cell lines that express H218 mRNA were loaded onto a SDS-PAGE gel and electrophoresed. The proteins were then transferred to nitrocellulose paper and reacted with a 1:500 dilution of purified antibody. Rabbit antibody was then detected with a labeled second-step reagent specific for rabbit antibody.

Cloning of the rat-edg cDNA A 1241 bp EcoRI-BamHI fragment of H2 cDNA was labeled with $^{32}$P by random hexamer priming and used to screen approximately 7.5×

$10^5$ cerebellar cDNAs of a rat cerebellar λ-ZAP library at medium stringency. The final hybridization wash was for 45 minutes at 47° C. in 2×SSC. Hybridizing clones were isolated for further evaluation. Purified clones were transferred into "BLUESCRIPT" plasmids (Stratagene) according to the manufacturer's protocol. Denatured double-stranded plasmids were sequenced by the dideoxy chain termination method (Sanger et al., 1977).

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

EXAMPLE 1
Cloning and Sequence Analysis of H218

A rat hippocampal cDNA library was screened at medium stringency with a rat D2 dopamine receptor cDNA. One of the hybridizing cDNAs, designated "H2", encodes all but a few amino-terminal residues of a novel G-protein coupled receptor. A cDNA, designated "18", encoding the remaining amino-terminal residues was isolated using a modified PCR technique. The H218 cDNA was prepared from the two independent, overlapping cDNA clones "H2" and "18" which were isolated as described above. The H2 and 18 cDNAs were spliced together to yield a 2.75 kb cDNA containing a complete 1056 bp ORF encoding 352 amino acids. The corresponding gene will be referred to herein as H218, and the encoded GPR protein as $p^{H218}$. The nucleotide sequence (SEQ ID NO.1) and the amino acid sequence (SEQ ID NO.2) that it encodes are shown in FIG. 1. The series of cytosines at the 5Q end of the clone result from the PCR procedure used to isolate the "18" cDNA. A database search revealed that $p^{H218}$ is clearly a member of the GPR superfamily (FIG. 2).

EXAMPLE 2
H218 mRNA Expression in Brain Tissue

Figure 3B:
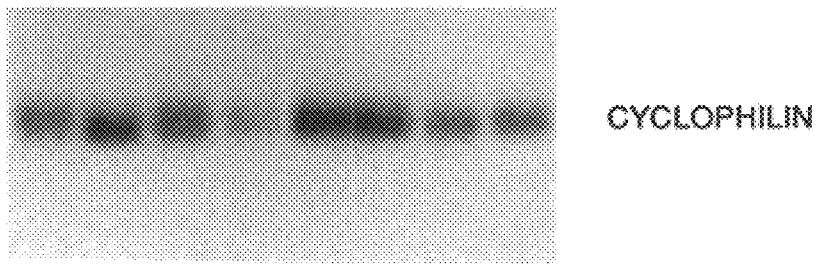

Poly-A RNA was extracted from whole rat brain at multiple stages of development ranging from embryonic day 12 (E12) to postnatal day 80 (P80; adult). A Northern blot of the rat RNA was probed with the complete H2 cDNA. The blot was washed at progressively higher stringencies and exposed to X-ray film after each wash. The autoradiograph revealed an approximately 3.2 kb transcript at all stages of development (FIG. 3). However, H218 mRNA levels are much higher during brain embryogenesis than during later periods of brain development. This pattern indicates that H218 plays a role in cell proliferation and/or differentiation, which is prevalent during brain embryogenesis, rather than in neurotransmission, which is prevalent later in brain development. However, the H218 gene may be involved during all of these processes.

The autoradiographs following the high stringency wash also contain other bands and/or smears, primarily in the E15 and E18 lanes. These signals displayed a preferential reduction in intensity (relative to the 3.2 kb band) during the series of progressively higher stringency washes leading up to the high stringency wash. Therefore, they most likely represent DNA contamination and/or abundant cross hybridizing mRNAs that are related, but not identical, to H218 mRNA. It is also possible that they may partially represent additional ontogenetically regulated H218 transcripts. However, in a smaller scale Northern blot experiment which examined only E15, E18, and P14 brain H218 mRNA, a single 3.2 kb band at E15 and E18 was detected.

EXAMPLE 3
H218 mRNA Expression in Other Tissue

Figure 4A:
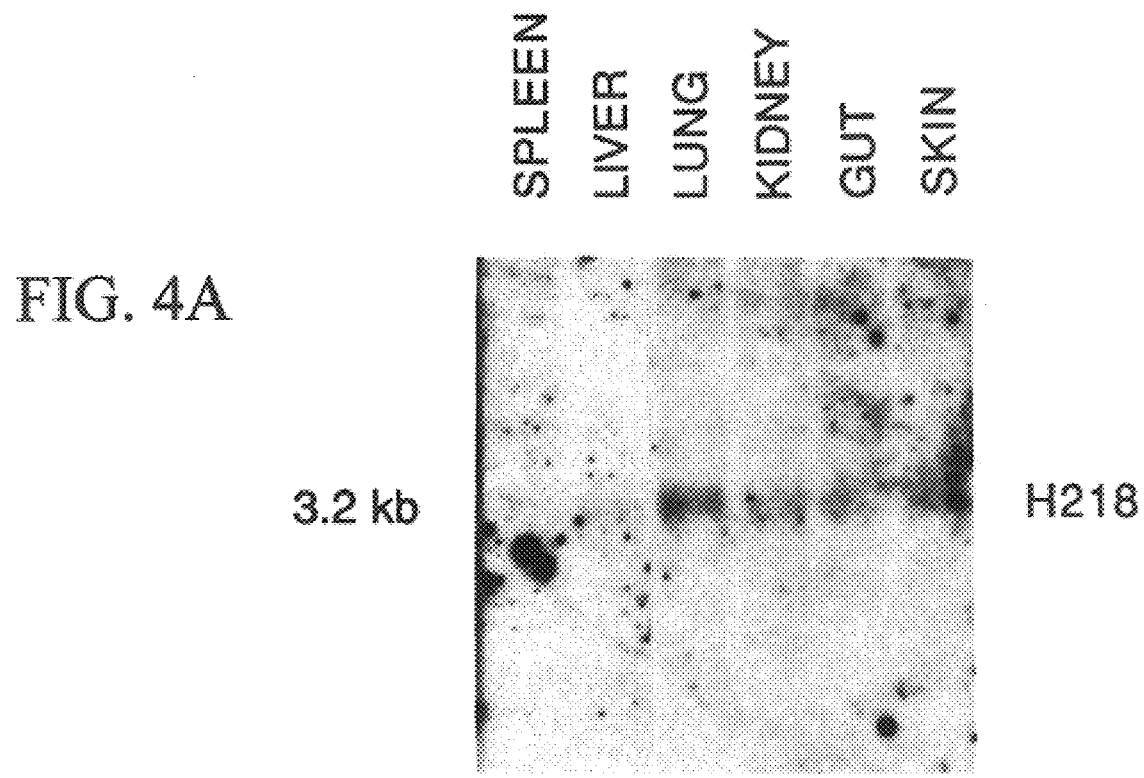
FIGS. 4A and 4B shows an X-ray autoradiograph of a Northern blot illustrating the distribution of H218 mRNA in various tissues of the postnatal day 14 rat. Approximately 20 μg of total RNA was loaded per lane. The blot was probed for H218 mRNA (panel A), stripped, and then probed for rat ribosomal RNA (panel B) as an extraction, loading, and transfer control.
Figure 4B:
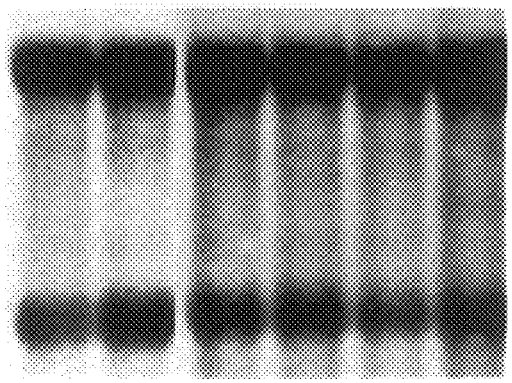

A Northern blot analysis of total RNA extracted from various organs of the postnatal day 14 (P14) rat was performed. The blot was probed with the H2 cDNA and washed at high stringency. A 3.2 kb H218 mRNA transcript was present in all tissues examined (FIG. 4). The H218 mRNA was most abundant in the lung. Less was found in the kidney, gut, and skin. A very low level of expression was detected in the spleen, brain and liver. This widespread distribution of H218 mRNA expression outside the brain at this stage of development is consistent with $p^{H218}$ role in cell proliferation and/or differentiation.

EXAMPLE 4
H218 mRNA Expression in Cell Lines

Northern blots were performed using poly-A RNA extracted from seven cell lines. The blots were probed with the H2 cDNA, washed at high stringency, and exposed to X-ray film. H218 mRNA was detected in all rodent cell lines examined. Thus, H218 mRNA is synthesized in B104 rat neuroblastoma cells, C6 rat glioma cells, PC12 rat pheochromocytoma cells, NB41A3 mouse neuroblastoma cells, D6P2T rat Schwannoma cells, NIH3T3 mouse fibroblasts, and RJK88 Chinese hamster fibroblasts. In all cases a prominent 3.2 kb band was observed after the high stringency wash, indicating that the sequence and size of the H218 mRNA transcript is highly conserved among mammals. The relative intensity of the band for each cell line is shown in Table 2.

TABLE 2

| Relative H218 mRNA concentrations in cell lines | |
| --- | --- |
| B104 rat neuroblastoma cells | +++ |
| PC12 rat pheochromocytoma cells | ++ |
| C6 rat glioma cells | +++ |
| D6P2T rat Schwannoma cells | ++ |
| NB41A3 mouse neuroblastoma cells | + |
| NIH3T3 mouse fibroblasts | ++ |
| RJK88 hamster fibroblasts | ++ |

Of the cells lines and tissue samples examined, H218 mRNA is most abundant in the B104 neuroblastoma cells and the C6 glioma cells. The presence of relatively high concentrations of H218 mRNA in these primitive transformed cells further confirms that the H218 gene is expressed in the early stages of development.

Figure 5A:
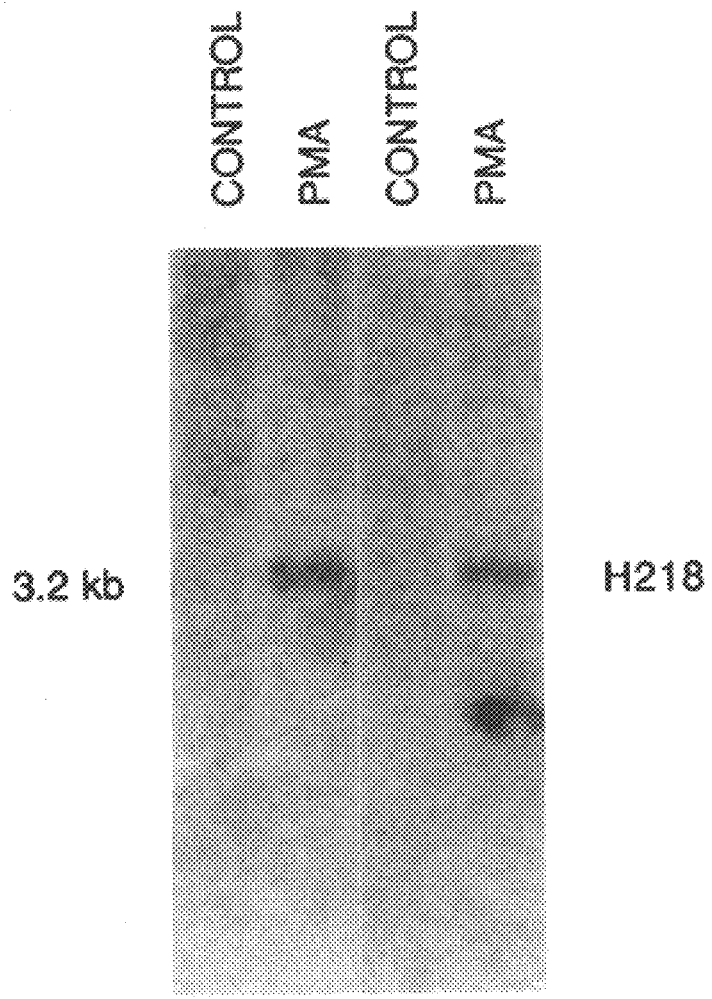
FIGS. 5A and 5B shows an X-ray autoradiograph of a Northern blot illustrating the effect of PMA treatment on H218 mRNA levels in RJK88 fibroblasts. Poly-A RNA was extracted from 2 independent 100 mm plates of cells treated with PMA for 2 hrs (PMA) or 2 parallel plates of cells treated with vehicle (CONTROL). The resulting blot was probed for H218 mRNA (panel A), stripped, and then probed for cyclophilin mRNA (panel B) as an extraction, loading, and transfer control. Lanes are presented in pairs based on their relative mRNA content (as indicated by the cyclophilin data).
Figure 5B:
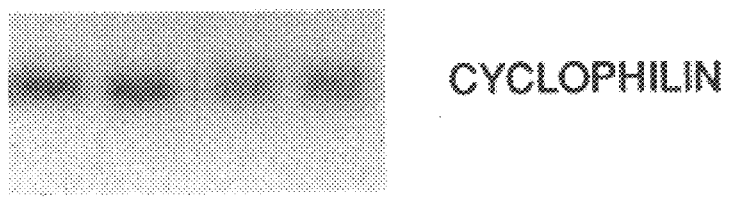

EXAMPLE 5
Manipulation of H218 mRNA Levels Using PMA and Nerve Growth Factor RJK88 Chinese hamster fibroblasts were grown to approximately 80% confluence in Dulbecco's Modified Eagle Media (DMEM) containing 10% fetal bovine serum (FBS). The cells were then "serum-deprived" in DMEM containing 0.5% FBS for 2 days and subsequently treated with phorbol 12-myristate 13-acetate (PMA) at a final concentration of 200 ng/ml. Poly-A RNA was extracted 2 hrs after the initiation of PMA treatment. Control RJK88 cells (processed in parallel with PMA treated cells) were grown, serum-deprived, treated with the vehicle for PMA and extracted. A Northern blot performed using the RNA was probed with the H2 cDNA and washed under high stringency conditions. H218 mRNA was undetectable in the serum-deprived, "quiescent" control cells but was clearly present in the cells treated with PMA (FIG. 5).

The nerve growth factor (NGF)-induced differentiation of PC12 rat pheochromocytoma cells from a phenotype resembling proliferating, immature adrenal chromaffin cells to a phenotype resembling differentiated sympathetic neurons has been widely employed as a model of neuronal differentiation. A Northern blot was used to determine whether H218 expression in PC12 cells is affected by NGF stimulation. PC12 cells were grown in RPMI media supplemented with 5% FBS and 10% horse serum. The cells were then serum-deprived in RPMI media containing 0.3% FBS and 0.7% horse serum and treated with NGF (50 ng/ml, 2.5 S) 24 hours later. Poly-A RNA was extracted following 1, 4, or 8 hours of the NGF treatment. Control cells (processed in parallel) were treated identically except they received NGF vehicle instead of NGF. A Northern blot using the RNA was probed with the H2 cDNA and washed at high stringency.

Figure 6A:
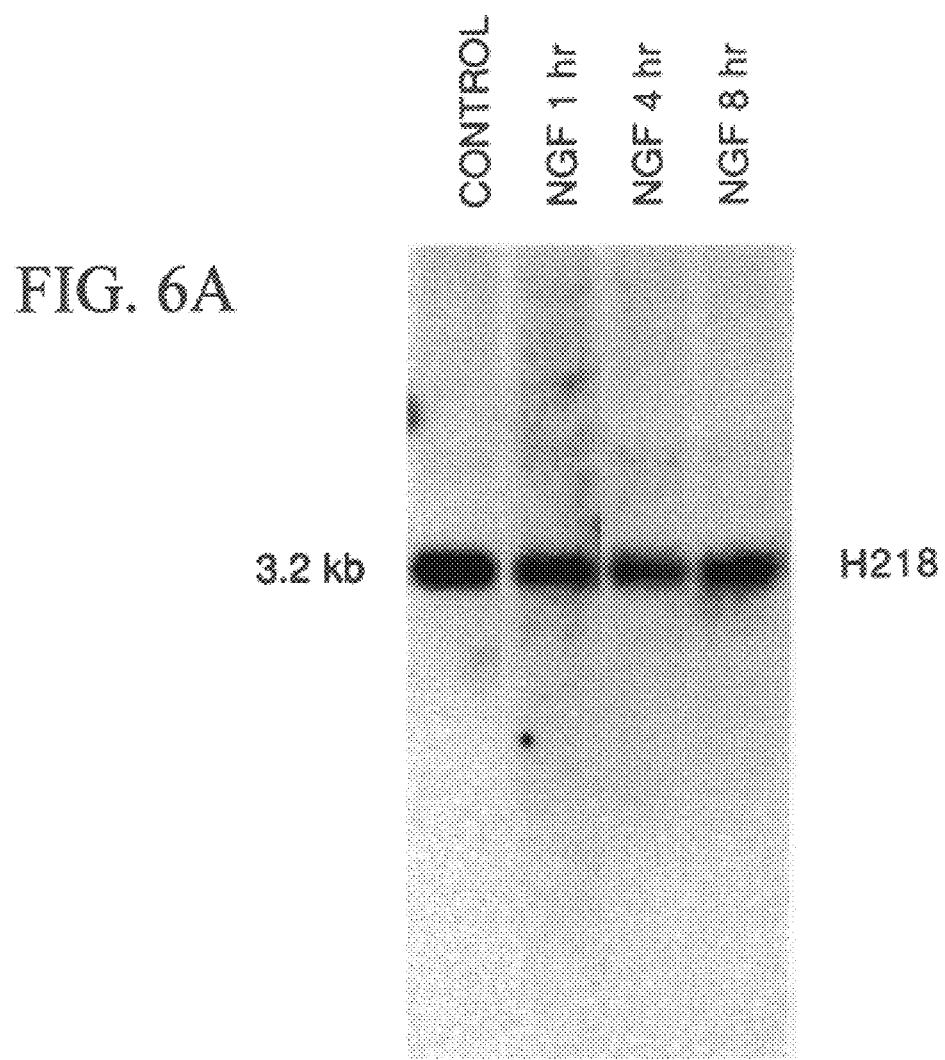
FIGS. 6A and 6B shows an X-ray autoradiograph of a Northern blot illustrating the effect of NGF treatment on H218 mRNA levels in PC12 cells. Poly-A RNA was extracted from 4 independent 100 mm plates of cells treated with NGF for either 1, 4, or 8 hrs or with a vehicle (CONTROL). The blot was probed for H218 mRNA (panel A), stripped, and then probed for cyclophilin mRNA (panel B) as an extraction, loading, and transfer control.
Figure 6B:
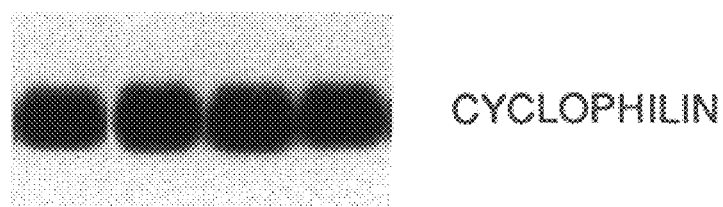

NGF treatment rapidly decreases H218 mRNA concentrations in PC12 cells (FIG. 6). H218 mRNA levels (densitometrically quantitated and normalized to cyclophilin mRNA levels) decreased by 39%, 54%, and 33% following NGF treatment of 1, 4, and 8 hours respectively, but returned to normal by 24 hours of continuous NGF treatment. The apparently transient nature of the H218 mRNA decrease in PC12 cells is unlikely the result of any NGF lability given that 1) NGF is a stable compound in solution and 2) PC12 cells treated with NGF that is only replenished every 2 to 3 days (when the media is exchanged) undergo a continuous differentiation which is reversible upon withdrawal of NGF.

EXAMPLE 6
Production and Characterization of Anti-$p^{H218}$ Antibodies

Rabbit antisera against four $p^{H218}$-derived synthetic peptides and having the amino acid sequences of SEQ ID NOS. 5, 6, 7, and 8, respectively, were prepared. All antisera specifically recognize, with high titers, the appropriate immunogen peptide by ELISA assay. One of the antisera, designated 1A, has been affinity purified. The purified 1A antiserum recognizes two $p^{H218}$ bands on Western blots of cell lines that express H218 mRNA. Both bands were eliminated when the antiserum was preincubated with the antigen peptide but not when it was preincubated with an equal concentration of an irrelevant control peptide.

In addition, the bands were clearly much more intense from a stable cell line that has been engineered to overexpress $p^{H218}$. The lower (apparent molecular weight of about 50–55 kDa), and weaker, band resulted from monomeric $p^{H218}$ molecules since it roughly corresponds in size to the deduced amino acid sequence encoded by the H218 mRNA open reading frame. The upper (apparent molecular weight of about 180–200 kDa) and more intense band most likely results from an aggregated form of the protein.

The antibody titer in rabbits injected with $p^{H218}$ peptide 1 (SEQ ID NO. 5) rises after the first few injections but drops thereafter, even with continued injections. This unexpected drop was not seen in the rabbits injected with other peptides. It is possible that the drop is the result of the anti-$p^{H218}$ antibodies in the rabbits blocking the function of $p^{H218}$ which, as discussed, may be involved in the cell proliferation events that are required for antibody production.

EXAMPLE 7
Construction and Characterization of Stable Cell Lines with Increased or Decreased Levels of $p^{H218}$ PC12 cells were transfected with either 1) a vector designed to synthesize H218 mRNA and thereby lead to overexpression of $p^{H218}$, 2) a vector designed to synthesize antisense H218 mRNA and thereby reduce expression of endogenous PC12 cell $p^{H218}$, or 3) the empty vector (as a control). Several stable cell lines derived from each condition were isolated and characterized.

Northern blot analyses indicate that all isolated cell lines designed to overexpress H218 mRNA do express additional H218 mRNA derived from the transfected DNA. The transfected DNA was designed so that the resulting H218 mRNA would differ in size from mature PC12 cell H218 mRNA and therefore can be easily distinguished. Western blot analysis on one of the lines expressing the most H218 mRNA indicate that this line expressed significantly more $p^{H218}$ than vector transfected control lines.

Nerve growth factor (NGF) and basic fibroblast growth factor (bFGF) cause PC12 cells to differentiate from a phenotype resembling proliferating, immature cells to a phenotype resembling differentiated sympathetic neurons. This system has been extensively studied as a model of neuronal development. The effects of NGF and bFGF on our stable cell lines were examined to determine if manipulating $p^{H218}$ levels affects PC12 cell differentiation. The morphology of the cell lines was qualitatively recorded in two identical experiments by an observer unaware of the identity of the cell lines. The two cell lines overexpressing the most H218 mRNA, including the line shown to overexpress $p^{H218}$, displayed a significantly less pronounced, growth factor induced change in cell body morphology when compared to vector transfected controls. Cell lines containing only a small amount of additional (exogenous DNA derived) H218 mRNA, including a line which does not detectably overexpress $p^{H218}$ by Western blot analysis, displayed cell morphology changes indistinguishable from vector transfected controls.

Cell lines transfected with the "antisense" vector displayed a significantly more pronounced growth factor induced change in cell body morphology when compared with vector transfected controls. Therefore, increasing $p^{H218}$ levels decreases differentiation while decreasing the expression of $p^{H218}$ increases cell differentiation.

EXAMPLE 8
Cloning of Human H218 Homolog

We have screened a human embryonic brain cDNA library using protocols as described for the cloning of the H218 cDNA and have isolated a cDNA which hybridizes under medium stringency conditions (two 45 minute washes at 42° C. in 2×SSC without formamide) to two non-overlapping fragments of the rat H218 cDNA. The pattern of restriction sites for this novel clone does not match the pattern of restriction sites found with the human edg cDNA clone, and is, therefore, a part of the human homolog of H218.

EXAMPLE 9
Cloning and Sequence Analysis of Rat-edg

Figure 7A:
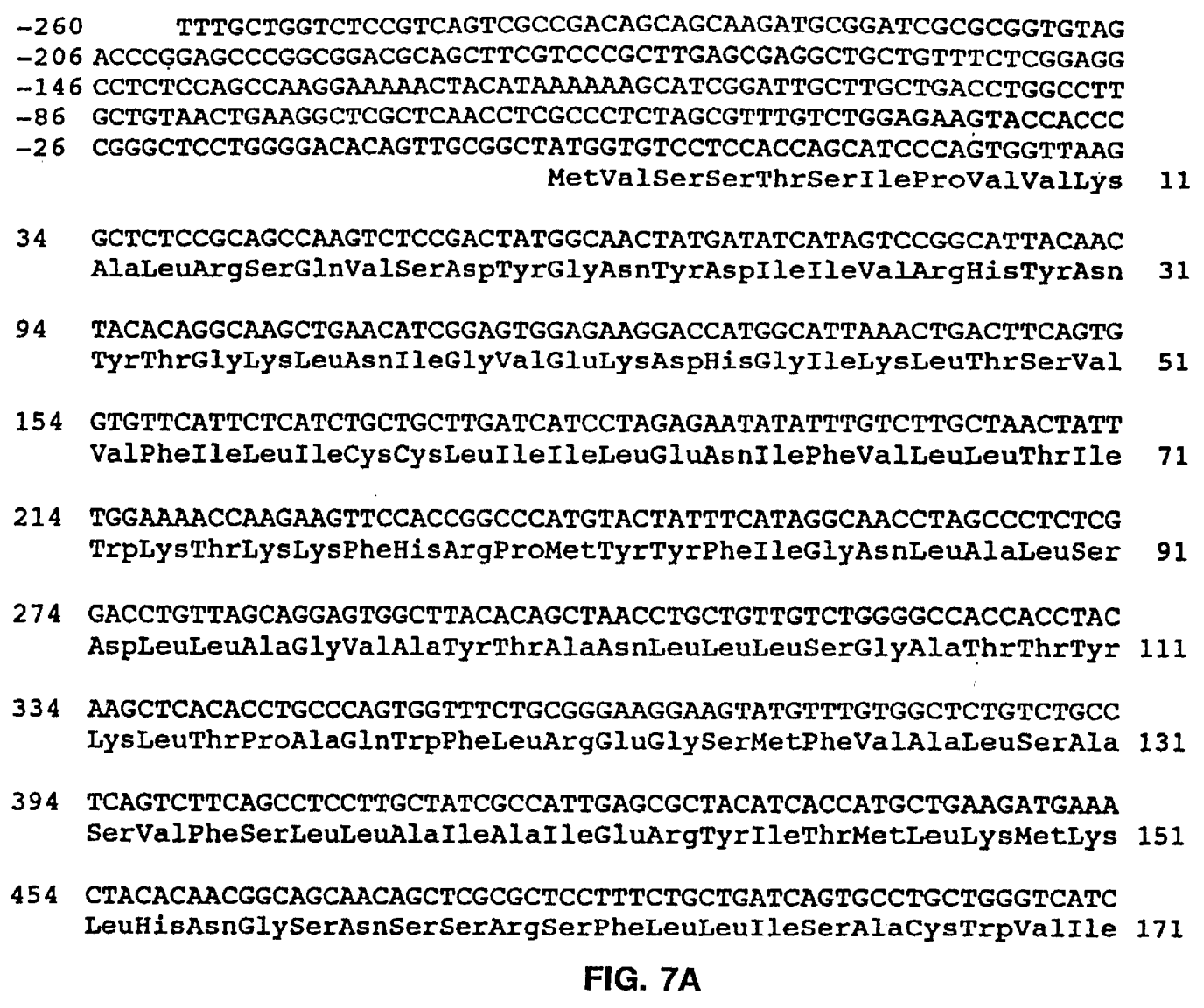

A rat cerebellar cDNA library was screened using the H2 cDNA fragment of H218. The largest hybridizing cDNA was completely sequenced (FIG. 7). This 2234 bp cDNA, designated rat-edg (SEQ ID NO.3), contains a 1149 bp ORF preceded by three in-frame stop codons. The cDNA contains an ATTTA motif in its 3Q untranslated region. This motif has been associated with mRNA degradation. The cDNA will subsequently be referred to herein as rat-edg (SEQ ID NO.3) and the encoded protein as $p^{rat\text{-}edg}$ (SEQ ID NO.4).

EXAMPLE 10
Expression of Rat-Edg in RNA in Tissue

The same Northern blot described in Example 2 was stripped and reprobed with the rat-edg cDNA. The blot was then washed at high stringency and exposed to X-ray film. Bands corresponding to an approximately 3.2 kb transcript were visible in all brain regions examined on the resulting autoradiograph. This size is close to the reported 3.0 kb size of human-edg. In contrast to H218 mRNA, the 3.2 kb rat-edg mRNA is preferentially expressed in later stages of postnatal development since a continual increase in mRNA expression is observed throughout development, with highest levels detected at P80. The 3.2 kb band observed following the high stringency wash was not the result of the rat-edg cDNA probe cross-hybridizing to H218 mRNA because: 1) the 3.2 kb transcript recognized by rat-edg displays a pattern of expression which is different from that of H218 mRNA, and 2) the in vitro transcribed H218 and rat-edg RNAs are specifically recognized on Northern blots by the appropriate probes.

A second set of generally weaker bands corresponding to a 4.9 kb transcript was also detected using the rat-edg cDNA. The 4.9 kb bands were not preferentially washed off during a series of progressively higher stringency washes and have been observed in multiple independent experiments. Therefore, they probably reflect an alternative rat-edg gene transcript. Interestingly, the expression of the 4.9 kb rat-edg RNA does not display an obvious trend during the developmental stages examined, and at E18, it is more abundant than the 3.2 kb transcript. In addition, the 4.9 kb rat-edg RNA was detected solely in brain RNA samples.

In addition, a Northern blot was performed with total RNA extracted from several regions of adult rat brain. The blot was probed with the rat-edg cDNA, washed at high stringency, and exposed to X-ray film. Rat-edg mRNA was comparably expressed in every region examined (i.e., the frontal cortex, striatum, ventral forebrain, hippocampus, cerebellum, and substantia nigra/ventral tegmental area). The 4.9 kb transcript may be preferentially expressed in the cerebellum, ventral forebrain, and frontal cortex.

The same Northern blot described in Example 3 was stripped and reprobed with the rat-edg cDNA. The blot was washed at high stringency and exposed to X-ray film. At P14, rat-edg mRNA is expressed in the lung (approximately the same concentration as adult brain) and at a much lower concentration in the liver, spleen, and possibly kidney. However, in contrast to H218 mRNA, rat-edg mRNA was not detected in the gut or skin. As noted above, no 4.9 kb bands are detected in any of these regions although they were visible in lanes of the same Northern that were loaded with brain RNA.

EXAMPLE 11
Expression of Rat-Edg RNA in Cell Lines

The Northern blots described in Example 4 were stripped and reprobed with rat-edg cDNA. They were subsequently washed at high stringency and exposed to X-ray film. Like H218 mRNA, rat-edg mRNA is expressed in NIH3T3 cells, C6 rat glioma cells, and rat PC12 pheochromocytoma cells. In contrast to H218 mRNA, rat-edg mRNA was not detected in RJK88 hamster fibroblasts, D6P2T rat Schwannoma cells, NB41A3 mouse neuroblastoma cells, or B104 neuroblastoma cells. Only the 3.2 kb transcript was detected in NIH3T3 and C6 cells, while only the 4.9 kb transcript is detected in PC12 cells.

It should be understood that the examples and embodiments described herein are for illustrative purposes only and that various modifications or changes in light thereof will be suggested to persons skilled in the art and are to be included within the scope and purview of this application and the scope of the appended claims.

REFERENCES

Bunemann, M., K. Liliom, B. K. Brandts, L. Pott, J-L. Tseng, D. M. Desiderio, G. Sun, D. Miller, G. Tigyi (1996) A novel membrane receptor with high affinity for lysosphingomyelin and sphingosine 1-phosphate in atrial myocytes. *EMBO J.* 15: 5527–5534.

Chirgwin, J. M., E. Przbyla, R. J. MacDonald, W. J. Rutter (1979) *Biochem.* 18: 5294–5299.

Devreotes, P. (1989) *Science* 245: 1054–1058.

Gutkind, J. S., E. A. Novotny, M. R. Brann, K. C. Robbins (1991) *Proc. Natl. Acad. Sci. USA* 88: 4703–4707.

Hanley, M. R. (1989) *Nature* 340: 97.

Julius, D., K. N. Huang, T. J. Livelli, R. Axel, T. M. Jessell (1990) *Proc. Natl. Acad. Sci. USA* 87: 928–932.

Julius, D., T. J. Livelli, T. M. Jessell, R. Axel (1989) *Science* 244: 1057–1062.

Kawa, S., S. Kimura, S-I. Hakomori, Y. Igarashi (1997) Inhibition of chemotactic motility and trans-endothelial migration of human neutrophils by sphingosine 1-phosphate. *FEBSLett.* 420: 196–200.

Loh, E. Y., J. F. Elliot, S. Cwirla, L. L. Lanier, M. M. Davis (1989) *Science* 243: 217–220.

MacLennan, A. J., G. D. Frantz, R. C. Weatherwax, N. J. K. Tillakaratne, A. J. Tobin (1990) *Molec. Cell. Neurosci.* 1: 151–160.

Postma, F. R., K. Jalink, T. Hengeveld, W. H. Moolenaar (1996) Sphingosine-1-phosphate rapidly induces rho-dependent neurite retraction: action through a specific cell surface receptor. *EMBO J.* 15: 2388–2395.

Sanger, F., S. Nicklen, A. R. Coulson (1977) *Proc. Natl. Acad. Sci. USA* 74: 5463–5467.

vanKoppen, C. J., D. M. zu Heringdorf, K. T. Laser, C. Zhang, K. H. Jakobs (1996) Activation of a high affinity $G_i$ protein-coupled plasma membrane receptor by sphingosine-1-phosphate. *J Biol. Chem.* 271: 2082–2087.

References Cont'd)

Yamamura, S. Y. Yatomi, F. Ruan, E. A. Sweeney, S-I. Hakomori, Y. Igarashi (1997) Sphingosine 1-phosphate regulates melanoma cell motility through a receptor-coupled extracelluar action and in a pertussis toxin-insensitive manner. *Biochemistry* 36: 10751–10759.

Yarden, Y., A. Ullrich (1998) *Ann. Rev. Biochem.* 57: 443–478.

Young, D., G. Waitches, C. Birchmeirer, O. Fasano, M. Wigler (1986) *Cell* 45: 711–719.

Zachary, I., P. J. Woll, E. Rozengurt (1987) *Dev Biol.* 124: 295–308.

I claim:

1. An isolated polynucleotide molecule selected from the group consisting of a polynucleotide which encodes a polypeptide comprising the amino acid sequence shown in SEQ ID NO. 16, and a polynucleotide which is complementary to a polynucleotide which encodes a polypeptide comprising the amino acid sequence shown in SEQ ID NO. 16.

2. An isolated polynucleotide comprising SEQ ID NO. 15.

\* \* \* \* \*